(12) United States Patent
Nishida et al.

(10) Patent No.: US 11,793,845 B2
(45) Date of Patent: Oct. 24, 2023

(54) COMPOSITION FOR AMELIORATING PERIPHERAL SENSORY NEUROPATHY

(71) Applicants: KINKI UNIVERSITY, Osaka (JP); KOBAYASHI PHARMACEUTICAL CO., LTD., Osaka (JP)

(72) Inventors: Shozo Nishida, Osaka (JP); Masanobu Tsubaki, Osaka (JP); Tomoya Takeda, Osaka (JP); Kiyotaka Okuno, Osaka (JP); Satoshi Wachi, Osaka (JP)

(73) Assignees: KINKI UNIVERSITY, Osaka (JP); KOBAYASHI PHARMACEUTICAL CO., LTD., Osaka (JP)

( * ) Notice: Subject to any disclaimer, the term of this patent is extended or adjusted under 35 U.S.C. 154(b) by 184 days.

(21) Appl. No.: 17/328,401

(22) Filed: May 24, 2021

(65) Prior Publication Data

US 2021/0275616 A1    Sep. 9, 2021

Related U.S. Application Data

(62) Division of application No. 16/470,811, filed as application No. PCT/JP2017/045547 on Dec. 19, 2017, now abandoned.

(30) Foreign Application Priority Data

Dec. 20, 2016  (JP) .................................. 2016-247143

(51) Int. Cl.

| A61K 36/07 | (2006.01) |
|---|---|
| A61P 25/02 | (2006.01) |
| A61P 35/00 | (2006.01) |
| A61K 33/243 | (2019.01) |
| A61K 9/00 | (2006.01) |
| A61K 31/337 | (2006.01) |
| A61K 31/381 | (2006.01) |
| A61K 31/4748 | (2006.01) |
| A61K 31/4965 | (2006.01) |

(52) U.S. Cl.
CPC ............ *A61K 36/07* (2013.01); *A61K 9/0056* (2013.01); *A61K 31/337* (2013.01); *A61K 31/381* (2013.01); *A61K 31/4748* (2013.01); *A61K 31/4965* (2013.01); *A61K 33/243* (2019.01); *A61P 25/02* (2018.01); *A61P 35/00* (2018.01)

(58) Field of Classification Search
None
See application file for complete search history.

(56) References Cited

U.S. PATENT DOCUMENTS

| 6,585,974 B1 | 7/2003 | Fujimura et al. |
| 6,919,081 B1 | 7/2005 | Asano et al. |
| 2013/0230560 A1 | 9/2013 | Tachibe et al. |
| 2019/0381120 A1 | 12/2019 | Nishida et al. |

FOREIGN PATENT DOCUMENTS

| EP | 0 292 601 A1 | 11/1988 |
| GB | 2359561 A | 8/2001 |
| GB | 2363570 A | 1/2002 |
| JP | H11-158080 A | 6/1999 |
| JP | 2000-159683 A | 6/2000 |
| JP | 2000-159686 A | 6/2000 |
| JP | 2003-155249 A | 5/2003 |
| JP | 2013-014549 A | 1/2013 |

OTHER PUBLICATIONS

Cassileth, Oncology, vol. 25, No. 6, vol. 25, Issue 6, May 6, 2011. (Year: 2011).*
Gaullier et al., "Supplementation with a Soluble Beta-Glucan Exported from Shiitake Medicinal Mushroom, *Lentinus edodes* (Berk.) Singer Mycelium: a Crossover, Placebo-Controlled Study in Healthy Elderly", *International Journal of Medicinal Mushrooms*, vol. 13, No. 4, pp. 319-326 (2011).
Ishitani, "Enhancement on Quality of Life by Lentinan", *The Clinical Report*, vol. 24, No. 6, pp. 3289-3296 (1990), along with a partial English-language translation.
Oishi et al., "Peripheral Neuropathy Induced by Anticancer Drugs", *Fukuoka Acta Medica*, vol. 104, No. 5, pp. 171-180 (2013), along with a partial English-language translation.
Shimoyama et al., "Cancerous Pain", *Journal of Clinical and Experimental Medicine*, vol. 195, No. 9, pp. 683-685 (2000), along with an English-language translation.
Kawamata et al., "Mechanisms Underlying Generation of Cancer Pain", *The Japanese Journal of Anesthesiology*, vol. 60, No. 9, pp. 1010-1017 (2011), including English-language abstract and partial English-language translation.
Higashiguchi et al., "Effect on Quality of Life of a *Lentinus endodes mycelia*-enriched Diet (L.E.M®) in Patients with Terminal Cancer", *Journal of Analytical Bio-science*, vol. 36, No. 2, pp. 153-160 (2013), along with a partial English-language translation.
International Search Report issued in PCT/JP2017/045547, dated Apr. 3, 2018, along with an English-language translation.

(Continued)

*Primary Examiner* — Melissa S Mercier
(74) *Attorney, Agent, or Firm* — GREENBLUM & BERNSTEIN, P.L.C.

(57) ABSTRACT

No drug has been available for treating a peripheral sensory neuropathy caused as a side effect by a drug, in particular, by an anticancer drug such as oxaliplatin.

A composition for ameliorating peripheral sensory neuropathy, which is characterized by including a *Lentinus edodes* mycelium extract, ameliorates symptoms induced by the drug such as the anticancer drug, including numbness of extremities, a pain in extremities, a reduction in deep tendon reflection, a reduction in muscle force, allodynia, hyperalgesia, impaired finger fine movement, impaired walking, stumbling, falling, impaired flexion (being difficult or impossible to sit on one's heels, sit cross-legged, sit with one's legs out to one side, sit on a chair, or the like), or paralysis of extremities.

8 Claims, 16 Drawing Sheets

(56) References Cited

OTHER PUBLICATIONS

Written Opinion of the ISA issued in PCT/JP2017/045547, dated Apr. 3, 2018, along with an English-language translation.

* cited by examiner

COMPOSITION FOR AMELIORATING PERIPHERAL SENSORY NEUROPATHY

The present application is a Divisional of U.S. application Ser. No. 16/470,811, which is the National Stage of International Patent Application No. PCT/JP2017/045547, filed Dec. 19, 2017, which claims priority to Japanese Patent Application No. 2016-247143, filed Dec. 20, 2016. The disclosures of each of the above-identified applications are expressly incorporated herein by reference in their entireties.

FIELD

The present invention relates to an amelioration composition for relieving, alleviating, or preventing a peripheral sensory neuropathy, and in particular, a composition for ameliorating the peripheral sensory neuropathy caused by an anticancer drug.

BACKGROUND

Drugs with various action mechanisms have been developed to be used in a chemotherapy for a malignant tumor. These drugs inhibit survival or proliferation of the tumor cell on the basis of specific action mechanisms. However, in general, these drugs not only act on the tumor cell, but also give the similar effect on a normal cell. Thus, taking the drug used in the chemotherapy causes a side effect such as hair loss, vomiting, a digestive tract disorder, hepatotoxicity, nephrotoxicity, and neurotoxicity along with the effect of inhibiting the tumor. Thus, a side-effect relieving drug for relieving these side effects has been demanded.

For example, Patent literature 1 discloses that cilnidipine or a pharmaceutically acceptable salt thereof relieves an organopathy caused by an anthracycline-based anticancer drug (adriamycin).

Further, Patent literature 2 discloses that an ingredient extracted from a mixture of a culture liquid in which the *Lentinus edodes* is cultured and a *Lentinus edodes* mycelium ameliorates symptoms of bone marrow toxicity caused by cyclophosphamide and 5-fluorouracil, hair loss and a digestive tract disorder caused by cytosine arabinoside, and a renal disorder induced by cisplatin.

CITATION LIST

Patent Literature

Patent Literature 1: Japanese Patent Application Laid-Open No. 2013-014549
Patent Literature 2: Japanese Patent Application Laid-Open No. Hei. 11-158080

SUMMARY

Technical Problem

The side effects of the drugs such as the anticancer drug cause many common symptoms, however, some symptoms are specific to the drugs. Administration of a DNA replication inhibitor (a platinum-based anticancer drug (oxaliplatin, etc.) and an alkylating agent), a microtubule-stabilizing agent (paclitaxel, etc.), a microtubule polymerization inhibitor (vincristine, etc.), or a proteasome inhibitor (bortezomib, etc.) causes a peripheral sensory neuropathy such as allodynia, hyperesthesia, or hypoesthesia as the side effect. These symptoms are specifically caused by the aforementioned drugs.

In particular, the peripheral sensory neuropathy is often developed with a symptom of a sensory neuropathy and causes a paresthesia accompanied by a spontaneous pain and an intense pain. A steady occurrence of such a symptom undesirably puts a stop to administration of the anticancer drug which has been therapeutically effective and impairs the quality of daily life of the patient, thus posing a significant problem. Further, no effective therapy for the peripheral sensory neuropathy induced by these anticancer drugs has yet been established to date.

Solution to Problems

The present invention has been conceived in view of the foregoing problems and provides a composition for ameliorating peripheral sensory neuropathy that ameliorates a side effect, namely, a peripheral sensory neuropathy induced by a drug such as an anticancer drug including oxaliplatin and paclitaxel.

More specifically, the composition for ameliorating the peripheral sensory neuropathy induced by the anticancer drug or the like according to the present invention is characterized by including a *Lentinus edodes* mycelium extract.

Advantageous Effects of Invention

The present invention can provide the composition for ameliorating peripheral sensory neuropathy. That is, administration of the *Lentinus edodes* mycelium extract can ameliorate a disorder induced by the cancer chemotherapy or the like such as numbness of extremities, a pain in extremities, a reduction in deep tendon reflection, a reduction in muscle force, allodynia, hyperalgesia, impaired finger fine movement, impaired walking, stumbling, falling, impaired flexion (being difficult or impossible to sit on one's heels, sit cross-legged, sit with one's legs out to one side, sit on a chair, or the like), or paralysis of extremities.

In order to manage the peripheral sensory neuropathy, it has been forced to reduce the amount of the anticancer drug or discontinue the chemotherapy until now. Using the composition of the present invention makes it possible to continue the appropriate cancer treatment, thereby leading to an early recovery from the cancer.

Further, the present invention, which provides the orally administrable composition for ameliorating peripheral sensory neuropathy that can be easily administered at home, is extremely convenient for the patient undergoing the cancer treatment at home. Further, the quality of life of the patient can be improved by ameliorating the peripheral sensory neuropathy caused by the cancer chemotherapy.

DESCRIPTION OF EMBODIMENTS

Figure 1:
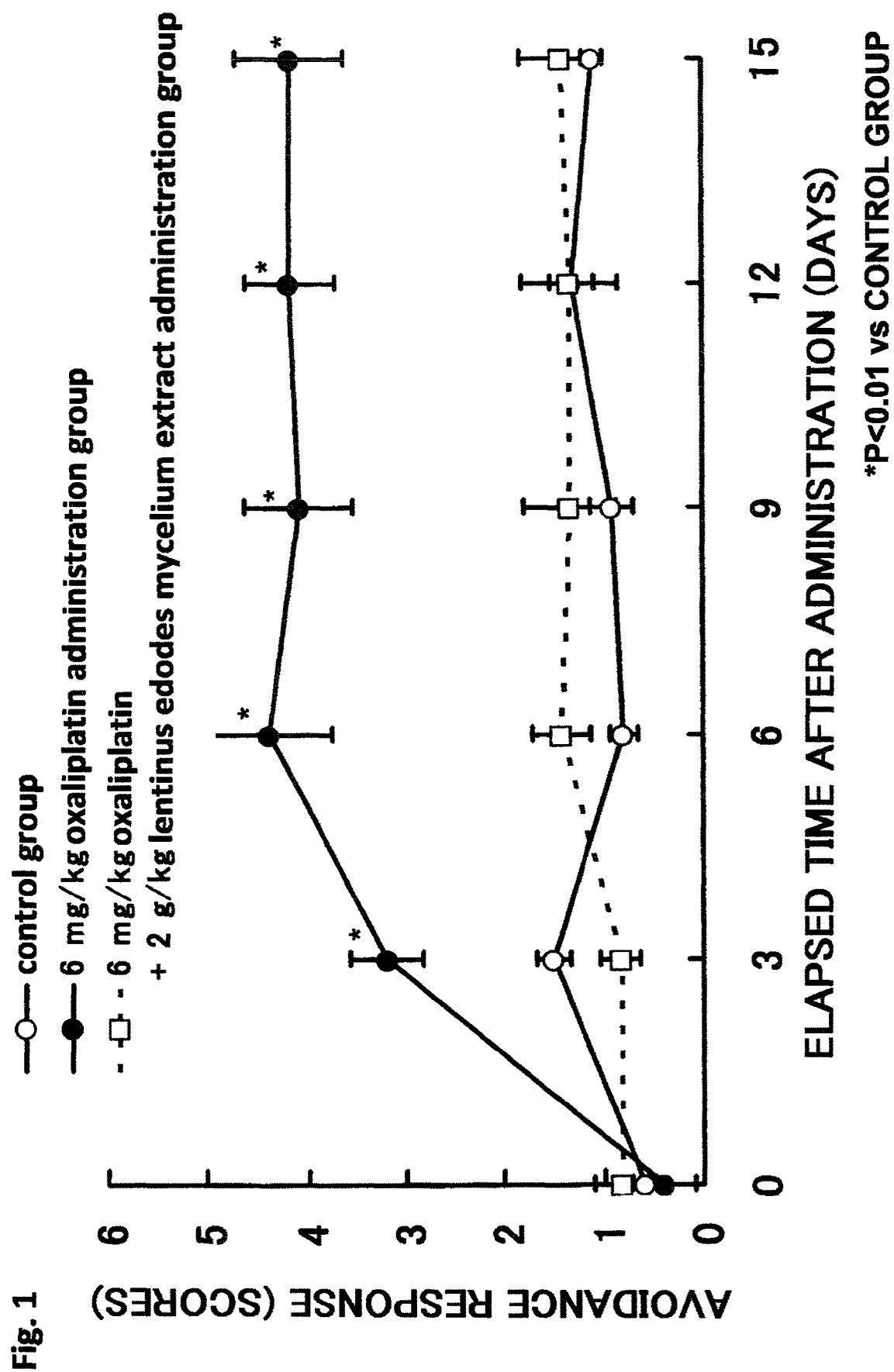
FIG. 1 is a diagram illustrating a result of a von Frey test in which a composition for ameliorating peripheral sensory neuropathy according to the present invention is coadministered with oxaliplatin.

The composition for ameliorating peripheral sensory neuropathy according to the present invention will be described below with reference to the drawings and examples. The following description exemplifies an embodiment and an example of the present invention, and the present invention is not limited to the following description. The following description may be modified without departing from the spirit of the present invention.

There is no particular limitation on "*Lentinus edodes* mycelium" serving as a raw material of a *Lentinus edodes* mycelium extract used in the composition for ameliorating peripheral sensory neuropathy according to the present invention. For example, a mycelium on the stage preceding a fruit body used as food can be used. In the present invention, for example, an extract obtained by culturing a *Lentinus edodes* in a solid medium (the *Lentinus edodes* mycelium extract) can be used. In the amelioration composition according to the present invention, the term "amelioration" not only means a radical treatment, but also means an effect of relieving, alleviating, or preventing a side effect caused by an anticancer drug or the like during the administration period.

The *Lentinus edodes* mycelium extract used in the composition for ameliorating peripheral sensory neuropathy according to the present invention can be prepared by a known method in the technical field, however, an extract obtained by crushing the mycelium, followed by extraction, can be used. Further, for example, an extract obtained by crushing and decomposing the solid medium including the mycelium in the presence of water can be used. As a solvent used for preparing the extract, for example, water, ethanol, methanol, butanol, isopropanol, and the like can be used. Water can be preferably used. The extraction can be performed by heating the solvent (e.g., about 85 to 105° C.), however, the extraction can be also performed at a lower temperature (e.g., 25 to 50° C., preferably 30 to 45° C.) by an ultrasonic treatment.

As the "*Lentinus edodes* mycelium extract", for example, an extract obtained by the following method can be used, although not limited thereto. That is, the *Lentinus edodes* is seeded on a solid medium having bagasse (a dry residue of sugarcane) and defatted rice bran as base materials. Next, the solid medium including the mycelia obtained by growing the mycelium is disentangled such that the amount of the 12-mesh passing disentangled solid medium becomes not more than 30 wt %. The disentangled solid medium was added with water and then crushed and grinded while being maintained at a temperature of 30 to 55° C., so that at least 70 wt % or more of the bagasse fibers pass through the 12-mesh sieve. Next, the 12-mesh passing products are heated to a temperature of 80° C., and a suspension-like liquid thus obtained is filtered to obtain a *Lentinus edodes* mycelium extract liquid.

In the present invention, the extract liquid obtained in this manner may be used as the *Lentinus edodes* mycelium extract as it is. However, for convenience, the extract liquid is concentrated and freeze dried, and stored as a powder, and such a powder is served in a variety of forms when used. The powder obtained by freeze drying is brown, hygroscopic and has a peculiar taste and odor.

The *Lentinus edodes* mycelium extract thus obtained contains 15 to 50%, preferably 20 to 40% (w/w) carbohydrates determined by carbohydrate analysis using the phenol-sulfuric acid method. Further, it contains 10 to 40%, preferably 13 to 30% (w/w) proteins determined by protein analysis using the Lowry method. Further, it contains 1 to 5%, preferably 2.5 to 3.5% (w/w) polyphenols determined by the Folin-Denis method using gallic acid as a standard. In addition to those, the *Lentinus edodes* mycelium extract contains about 0.1% fats, about 0.4% fibers, and about 20% ashes.

Further, an example of the constituting sugar composition (mass %) of the *Lentinus edodes* mycelium extract obtained as described above is as follows. Note that this composition may vary depending on culture conditions and the like.

Xylose: 15.2; arabinose: 8.2; mannose: 8.4; glucose: 39.4; galactose: 5.4; amino sugar (glucosamine): 12.0; uronic acid: 11.3.

The composition for ameliorating peripheral sensory neuropathy according to the present invention includes the aforementioned *Lentinus edodes* mycelium extract. The content ratio of the *Lentinus edodes* mycelium extract in the composition for ameliorating peripheral sensory neuropathy is not particularly limited. It can be appropriately changed depending on a subject to be administered (including an animal) and a symptom (a cause). However, it is desirable that the composition for ameliorating peripheral sensory neuropathy includes the *Lentinus edodes* mycelium extract in an amount of at least 10 mass % or more, preferably 20 mass % or more, most preferably 30 mass % or more. The *Lentinus edodes* mycelium extract in the composition for ameliorating peripheral sensory neuropathy may be 100 mass %.

The composition for ameliorating peripheral sensory neuropathy can be provided as a therapeutic agent (a medical composition) for the peripheral sensory neuropathy. As the medical composition, the composition according to the present invention can exhibit its effect by oral administration. Thus, it can be provided as an internal preparation. For example, the composition for ameliorating peripheral sensory neuropathy in a power form can be formulated into a capsule, a granule, a powder, a tablet, and the like, and provided. When used as an oral agent, the composition can be added with an additive such as a binder, a lubricant, a disintegrator, a colorant, a flavoring agent, an antiseptic, an antioxidant, and a stabilizer, and the oral agent can be produced in a form of a capsule, a granule, a powder, and a tablet by a routine method.

Further, the medical composition according to the present invention may be formulated into an external preparation such as a liquid, an ointment, a cream, a gel, a stick, and an aerosol, and the external preparation may be parenterally administered. When used as the external preparation, the composition can be compounded with water, a lower alcohol, a solubilizer, a surfactant, an emulsion stabilizer, a gelling agent, an adhesive, and other necessary base ingredients. Further, an additive such as a vasodilator, adrenocortical hormone, a keratolytic agent, a moisturizing agent, a bactericide, an antioxidant, a refreshing agent, a perfume, and a coloring matter may be appropriately compounded.

It is desirable that the medical composition according to the present invention include the *Lentinus edodes* mycelium extract in an amount of at least 10 mass % or more, preferably 20 mass % or more, and most preferably 30 mass % or more. Further, the *Lentinus edodes* mycelium extract in the medical composition may be 100 mass %.

Further, the composition for ameliorating peripheral sensory neuropathy according to the present invention can be provided as a processed food. That is, the composition for ameliorating peripheral sensory neuropathy according to the present invention taken as the processed food exhibits an effect equivalent to that of the amelioration composition according to the present invention.

Examples of the processed food include not only a general processed food including a favorite food and health food such as a candy, chewing gum, jelly, a biscuit, a cookie, a rice cracker, bread, a noodle, a fish/meat paste product, tea, a refreshing beverage, a coffee beverage, a milk beverage, a whey beverage, a lactic acid bacteria beverage, yogurt, ice cream, and pudding, but also foods with health claims such as foods for specified health uses and foods with nutrient function claims specified in the regulatory system "Foods with Health Claims" by the Ministry of Health, Labour, and Welfare, Japan. Furthermore, a dietary supplement (a supplement), feed, a food additive, and the like are also included in the processed food.

The processed food according to the present invention can be prepared by adding the composition for ameliorating peripheral sensory neuropathy (the *Lentinus edodes* mycelium extract) in raw materials of these processed foods. It is desirable that the processed food according to the present invention include the *Lentinus edodes* mycelium extract in an amount of at least 10 mass % or more, preferably 20 mass % or more, most preferably 30 mass % or more.

The intake amount of the composition in the present invention can be appropriately selected depending on the symptom, age, weight, an elapsed time after onset of symptom, a therapeutic treatment performed together, and the like. In an example of the present invention, in a case where a mouse is administered with the anticancer drug in an amount of 6 mg/kg mouse body weight, the daily intake amount of the dried powder of the *Lentinus edodes* mycelium extract effective for ameliorating the peripheral sensory neuropathy is 0.02 g (that is, 1.0 g/kg mouse body weight considering that the average body weight of mice is 20 g).

In the technical field, it is known that, when an ingredient is effective in mice, the effective amount of the ingredient expressed as per kg body weight corresponds to an effective dose ingested per day by a human adult male weighing 60 kg. Further, the dose of the anticancer drug in human is generally one third to equal to the dose of the anticancer drug expressed as per kg mouse body weight in the present example.

Thus, the effective amount of the dried powder of the *Lentinus edodes* mycelium extract ingested per day by a human adult male is preferably 0.3 g or more, more preferably 0.3 g to 30.0 g/day/adult, most preferably 0.6 g to 24.0 g/day/adult. Note that the term "X to Y" described herein refers to a range between "X or more and Y or less".

Note that the *Lentinus edodes* mycelium extract according to the present invention is administered to a subject to be administered as the composition for ameliorating peripheral sensory neuropathy, and thus it may also be considered as a method for ameliorating the peripheral sensory neuropathy. In this case, the composition for ameliorating peripheral sensory neuropathy may be the *Lentinus edodes* mycelium extract itself. That is, the composition for ameliorating peripheral sensory neuropathy may be constituted 100% by the *Lentinus edodes* mycelium extract.

EXAMPLES

<Culture of *Lentinus edodes* Mycelium>

A medium used for culturing the *Lentinus edodes* mycelium was prepared by adding an appropriate amount of pure water to a solid medium including 80 parts by weight of bagasse and 10 parts by weight of defatted rice bran. The *Lentinus edodes* mycelium was seeded on this medium and placed in a culture room where the interior temperature and humidity are controlled to propagate the mycelium.

<Production of Dried Powder of *Lentinus edodes* Mycelium Extract>

To the medium in which the *Lentinus edodes* mycelium was spread, eight equivalents of pure water was added. The medium was crushed, heated to 80° C. for 2 hours by a jacket preheater, subjected to liquid circulation extraction, and then filtered. The filtered extract was concentrated so as to obtain a Brix value of 27%±2%. The concentrated extract was sterilized at 135° C. for 15 seconds using an instantaneous heating sterilizer, and the sterilized extract was added with sterile water so as to adjust the Brix value to 25%±2% and then subjected to freeze drying. This freeze-dried powder was crushed and then allowed to pass through a 42-mesh sieve to obtain the dried powder of the *Lentinus edodes* mycelium extract.

(Example 1) <Effect on Peripheral Sensory Neuropathy Induced by Oxaliplatin in Mice>

The effect of the *Lentinus edodes* mycelium extract on hyperesthesia such as allodynia (an intense pain caused by tactile stimulation that usually does not induce the pain) to mechanical stimulation and paresthesia to cold stimulation induced by administration of oxaliplatin as the anticancer drug was examined. Oxaliplatin is a platinum preparation (a platinum-based anticancer drug) that inhibits DNA replication. The *Lentinus edodes* mycelium extract was orally administered to mice and the following tests (a cold plate test and a von Frey test) were performed.

(1) Administration of Test Object

Male Balb/c mice of 6 to 7 weeks old were used. The mice were divided into three groups: a control group, an oxaliplatin administration group, and an oxaliplatin and *Lentinus edodes* mycelium extract administration group (oxaliplatin+*Lentinus edodes* mycelium extract administration group). Oxaliplatin was administered to each mouse once a day at a dose of 6 mg/kg. Further, the *Lentinus edodes* mycelium extract was administered to each mouse once a day at a dose of 2 g/kg.

Further, the number of times of administration was set to once a week (on Day 0, Day 7, and Day 14) for oxaliplatin and daily (from Day 0 to Day 15) for the *Lentinus edodes* mycelium extract in both the von Frey test and the cold plate test below.

(2) Von Frey Test

The mice in the three groups in the above (1) were put in a cage and a filament having a strength of 0.16 g was pressed on the plantar surface of the leg to measure the number of times (a score) of avoidance response. The result is shown in FIG. 1.

Referring to FIG. 1, the horizontal axis indicates an elapsed time after administration (days) and the vertical axis indicates the avoidance response (scores). The higher number of times of avoidance means that the mouse avoids the stimulation by the filament more. Open circles with a solid line represent the control group. Filled circles with a solid line represent the group in which only oxaliplatin was administered. Open squares with a dash line represent the group in which oxaliplatin and the *Lentinus edodes* mycelium extract were administered. When the difference with the control group was determined to be significant using a significance level of 5%, the data were marked by "*".

In the oxaliplatin administration group (filled circles with a solid line), the avoidance response score significantly increased three days after the administration as compared with the control group (open circles with a solid line). This suggests that the peripheral sensory neuropathy was developed by the administration of oxaliplatin. On the other hand, the group in which the *Lentinus edodes* mycelium extract was coadministered (oxaliplatin+*Lentinus edodes* mycelium extract administration group: open squares with a dash line) showed the avoidance response score of the same level as that in the control group. In the oxaliplatin+*Lentinus edodes* mycelium extract administration group, an increase in the avoidance response score was suppressed as compared with that in the oxaliplatin administration group (filled circles with a solid line).

Further, it was found that, in the oxaliplatin+*Lentinus edodes* mycelium extract administration group (open squares with a dash line), suppression of the decrease in the pain threshold was continued even after finishing the administration of the *Lentinus edodes* mycelium extract (on Day 16 or later).

(3) Cold Plate Test

The effect of the *Lentinus edodes* mycelium extract on the paresthesia to cold stimulation was tested by performing the cold plate test. The mice in the three groups in the above (1) were put on a cold plate set to 10° C. and a response time for avoidance (a latency) was measured. The shorter latency means that the mouse avoids the cold stimulation of the cold plate more. The result is shown in FIG. 2.

Figure 2:
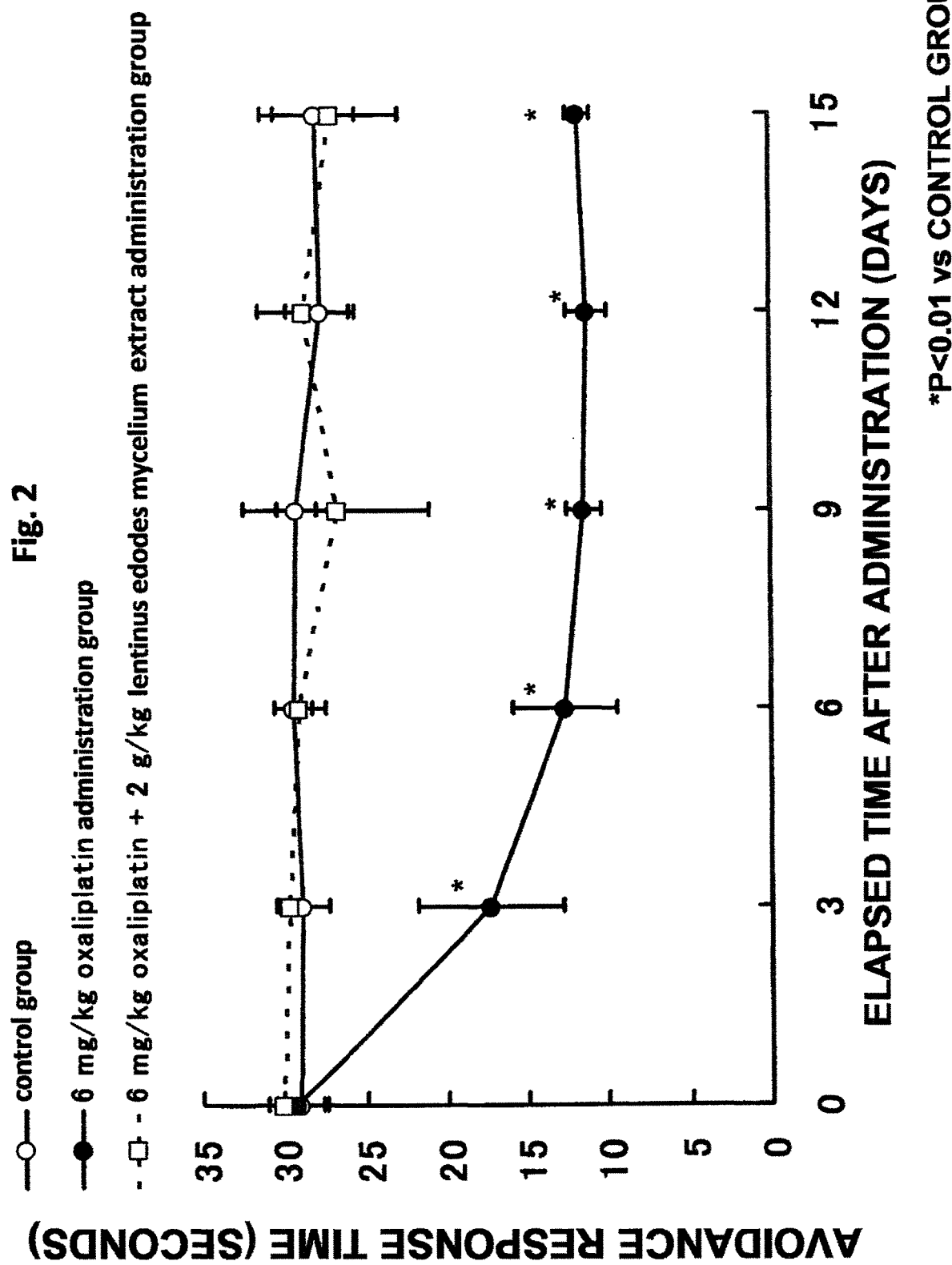
FIG. 2 is a diagram illustrating a result of a cold plate test in which the composition for ameliorating peripheral sensory neuropathy according to the present invention is coadministered with oxaliplatin.

Referring to FIG. 2, the horizontal axis indicates the elapsed time after administration (days) and the vertical axis indicates the avoidance response time (seconds). Open circles with a solid line represent the control group. Filled circles with a solid line represent the group in which only oxaliplatin was administered. Open squares with a dash line represent the group in which oxaliplatin and the *Lentinus edodes* mycelium extract were administered (oxaliplatin+*Lentinus edodes* mycelium extract administration group). When the difference with the control group was determined to be significant using a significance level of 5%, the data were marked by "*".

On Day 3 in the test, the latency to the cold stimulation of the cold plate was significantly reduced in the oxaliplatin administration group (filled circles with a solid line). This suggests that the peripheral sensory neuropathy was developed by the administration of oxaliplatin. On the other hand, the oxaliplatin+*Lentinus edodes* mycelium extract administration group (open squares with a dash line) showed the latency of about the same level as that in the control group (open circles with a solid line), and thus the decrease in the latency was suppressed as compared with that in the oxaliplatin administration group (filled circles with a solid line).

From the above results, it can be concluded that the *Lentinus edodes* mycelium extract ameliorates the symptom of the peripheral nervous erethism induced by oxaliplatin.

(Example 2) <Effect on Peripheral Sensory Neuropathy Induced by Paclitaxel in Mice>

The effect of the *Lentinus edodes* mycelium extract of the present invention on hyperesthesia such as allodynia to mechanical stimulation and paresthesia to cold stimulation induced by administration of paclitaxel as the anticancer drug was examined. Paclitaxel is a taxane-based anticancer drug that inhibits microtubule polymerization during cell division by stabilizing a microtubule. The *Lentinus edodes* mycelium extract of the present invention was orally administered to mice, and the tests (the cold plate test and the von Frey test) were performed in the same manner as in Example 1.

(1) Administration of Test Object

Male Balb/c mice of 6 to 7 weeks old were used as in Example 1. The mice were divided into three groups: a control group, a paclitaxel administration group, and a paclitaxel and *Lentinus edodes* mycelium extract administration group (paclitaxel+*Lentinus edodes* mycelium extract administration group). Paclitaxel was administered to each mouse once a day at a dose of 6 mg/kg. Further, the *Lentinus*

*edodes* mycelium extract was administered to each mouse once a day at a dose of 2 g/kg.

Further, the number of times of administration was set to once a week (on Day 0, Day 7, and Day 14) for paclitaxel and daily (from Day 0 to Day 15) for the *Lentinus edodes* mycelium extract in both the von Frey test and the cold plate test below.

(2) Von Frey Test

Figure 3:
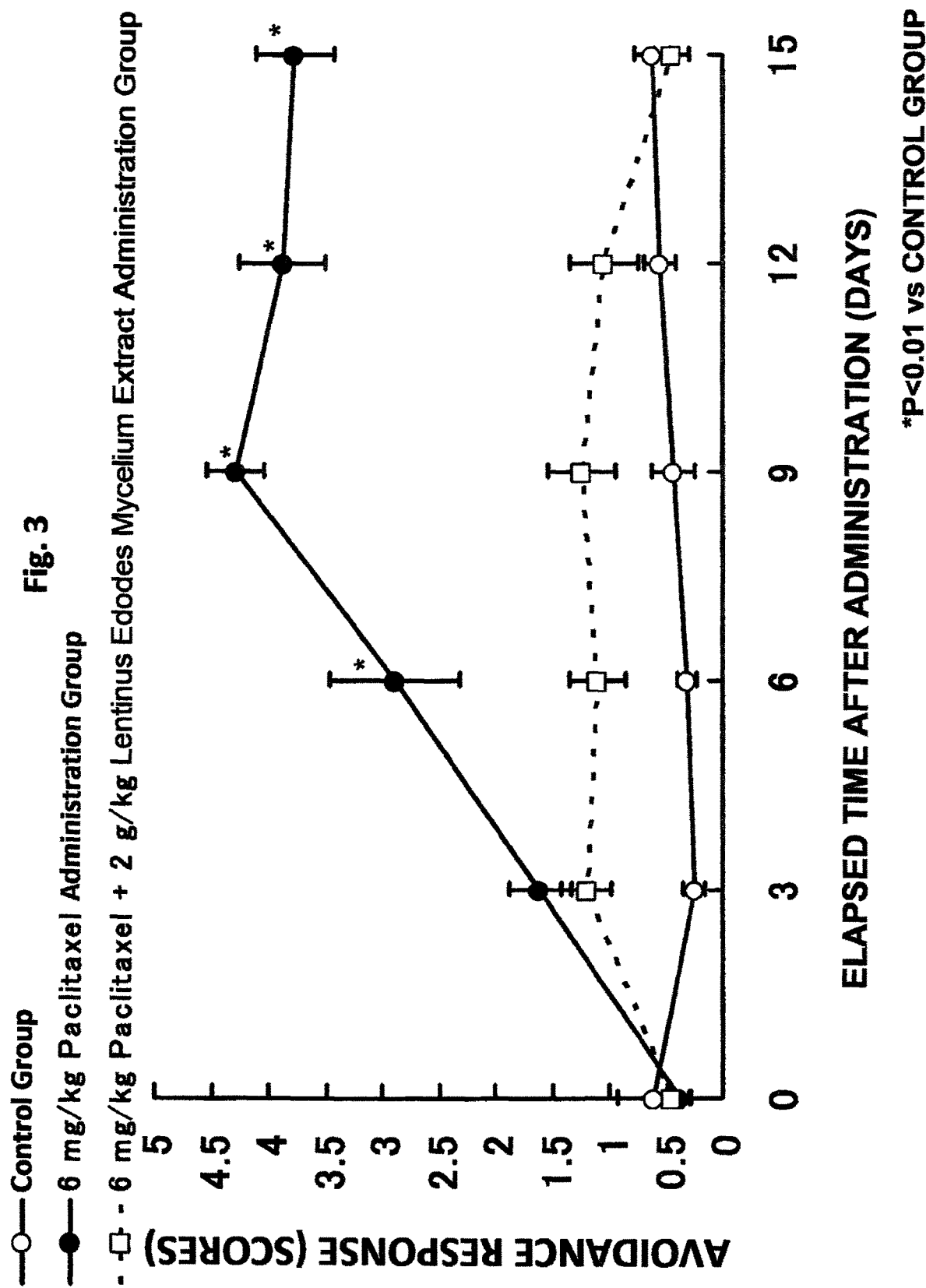
FIG. 3 is a diagram illustrating a result of the von Frey test in which the composition for ameliorating peripheral sensory neuropathy according to the present invention is coadministered with paclitaxel.

Evaluation was performed in the same manner as in the test with oxaliplatin. The result is shown in FIG. 3. Referring to FIG. 3, the horizontal axis indicates an elapsed time after administration (days) and the vertical axis indicates the avoidance response (scores). Open circles with a solid line represent the control group. Filled circles with a solid line represent the group in which only paclitaxel was administered. Open squares with a dash line represent the group in which paclitaxel and the *Lentinus edodes* mycelium extract were administered (paclitaxel+*Lentinus edodes* mycelium extract administration group). When the difference with the control group was determined to be significant using a significance level of 5%, the data were marked by "*".

In the paclitaxel administration group (filled circles with a solid line), the avoidance response score significantly increased three days after the administration as compared with the control group (open circles with a solid line). This suggests that the peripheral sensory neuropathy was developed by the administration of paclitaxel. On the other hand, the group in which paclitaxel and the *Lentinus edodes* mycelium extract were coadministered (paclitaxel+*Lentinus edodes* mycelium extract administration group: open squares with a dash line) showed the avoidance response score of the same level as that in the control group. In the paclitaxel+*Lentinus edodes* mycelium extract administration group, the increase in the avoidance response score was suppressed as compared with that in the paclitaxel administration group (filled circles with a solid line).

Further, it was found that, in the paclitaxel+*Lentinus edodes* mycelium extract administration group (open squares with a dash line), suppression of the decrease in the pain threshold was continued even after finishing the administration of the *Lentinus edodes* mycelium extract (on Day 16 or later).

(3) Cold Plate Test

In the present test, the mice were divided into four groups by a difference in test objects. As in Example 1, male Balb/c mice of 6 to 7 weeks old were used. The mice were divided into a total of four groups, a control group, a paclitaxel administration group, and two different paclitaxel and *Lentinus edodes* mycelium extract administration groups (paclitaxel+*Lentinus edodes* mycelium extract administration groups). Paclitaxel was administered to each mouse once a day at a dose of 6 mg/kg. Further, a group in which the *Lentinus edodes* mycelium extract was administered to each mouse once a day at a dose of 1 g/kg (hereinafter referred to as "1 g/kg administration group") and a group in which the *Lentinus edodes* mycelium extract was administered to each mouse once a day at a dose of 2 g/kg (hereinafter referred to as "2 g/kg administration group") were prepared.

Figure 4:
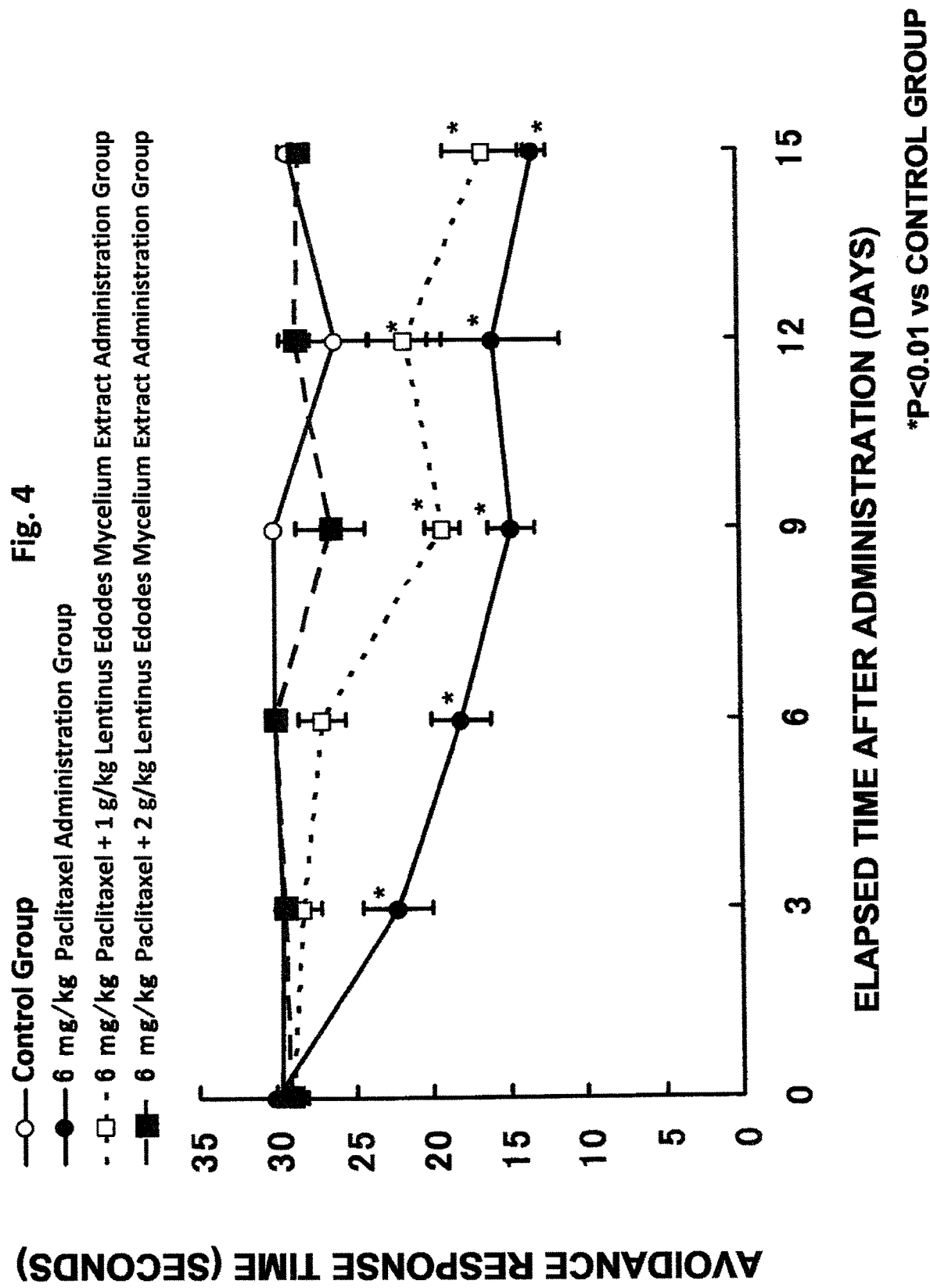
FIG. 4 is a diagram illustrating a result of the cold plate test in which the composition for ameliorating peripheral sensory neuropathy according to the present invention is coadministered with paclitaxel.

Evaluation was performed in the same manner as in the test with oxaliplatin. The result is shown in FIG. 4. Referring to FIG. 4, the horizontal axis indicates the elapsed time after administration (days) and the vertical axis indicates the avoidance response time (seconds). Open circles with a solid line represent the control group. Filled circles with a solid line represent the group in which only paclitaxel was administered. Open squares with a dash line and filled squares with a dash line represent the groups in which paclitaxel and the *Lentinus edodes* mycelium extract were administered at the same time (paclitaxel+*Lentinus edodes* mycelium extract administration groups). The open squares with a dash line indicate the 1 g/kg administration group, while the filled squares with a dash line indicate the 2 g/kg administration group. When the difference with the control group was determined to be significant using a significance level of 5%, the data were marked by "*".

Referring to FIG. 4, on Day 3 in the test, the latency to the cold stimulation of the cold plate was significantly reduced in the paclitaxel administration group (filled circles with a solid line). This suggests that the peripheral sensory neuropathy was developed by the administration of paclitaxel. On the other hand, the 2 g/kg administration group (filled squares with a dash line) of the paclitaxel+*Lentinus edodes* mycelium extract co-administration groups showed the latency of about the same level as that in the control group (open circles with a solid line). Thus, the decrease in the latency was suppressed in the 2 g/kg administration group as compared with that in the paclitaxel administration group (filled circles with a solid line).

Further, the decrease in the latency was suppressed in the 1 g/kg administration group (open squares with a dash line) of the groups in which paclitaxel and the *Lentinus edodes* mycelium extract were coadministered as compared with that in the group in which only paclitaxel was administered (filled circles with a solid line).

(Example 3) <Effect on Peripheral Sensory Neuropathy Induced by Vincristine in Mice>

The effect of the *Lentinus edodes* mycelium extract of the present invention on hyperesthesia such as allodynia to mechanical stimulation and paresthesia to cold stimulation induced by administration of vincristine as the anticancer drug was examined. Vincristine inhibits cell mitosis by inhibiting a polymerization reaction of a microtubule. The *Lentinus edodes* mycelium extract of the present invention was orally administered to mice, and the tests (the cold plate test and the von Frey test) were performed in the same manner as in Example 1.

(1) Administration of Test Object

In the present test, the mice were divided into three groups by a difference in test objects. As in Example 1, male Balb/c mice of 6 to 7 weeks old were used. The mice were divided into a total of three groups, a control group, a vincristine administration group, and a vincristine and *Lentinus edodes* mycelium extract administration group (vincristine+*Lentinus edodes* mycelium extract administration group).

Vincristine was administered to each mouse once a day at a dose of 0.2 mg/kg. Further, the *Lentinus edodes* mycelium extract was administered to each mouse once a day at a dose of 2 g/kg.

Further, the number of times of administration was set to once a week (on Day 0, Day 7, and Day 14) for vincristine and daily (from Day 0 to Day 15) for the *Lentinus edodes* mycelium extract in both the von Frey test and the cold plate test below.

(2) Von Frey Test

Figure 5:
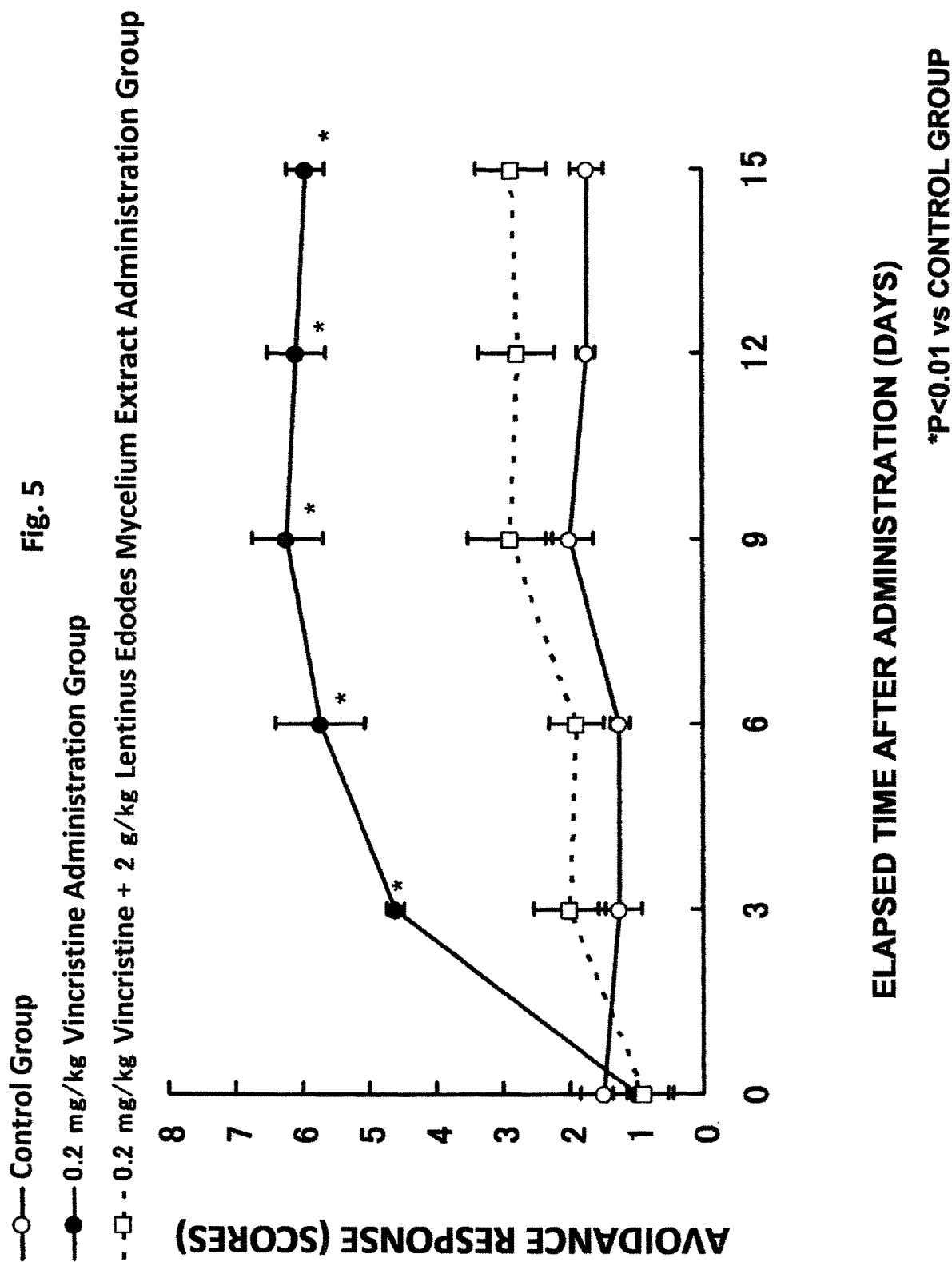
FIG. 5 is a diagram illustrating a result of the von Frey test in which the composition for ameliorating peripheral sensory neuropathy according to the present invention is coadministered with vincristine.

Evaluation was performed in the same manner as in the test with oxaliplatin in Example 1. The result is shown in FIG. 5. Referring to FIG. 5, the horizontal axis indicates an elapsed time after administration (days) and the vertical axis indicates the avoidance response (scores). Open circles with a solid line represent the control group. Filled circles with a solid line represent the group in which only vincristine was administered. Open squares with a dash line represent the group in which vincristine and the *Lentinus edodes* mycelium extract were administered at the same time (vincristine+*Lentinus edodes* mycelium extract administration group). When the difference with the control group was determined to be significant using a significance level of 5%, the data were marked by "*".

In the vincristine administration group (filled circles with a solid line), the avoidance response score significantly increased three days after the administration as compared with the control group (open circles with a solid line). This suggests that the peripheral sensory neuropathy was developed by the administration of vincristine. On the other hand, the vincristine+*Lentinus edodes* mycelium extract administration group (open squares with a dash line) showed the avoidance response score of the same level as that in the control group. In the vincristine+*Lentinus edodes* mycelium extract administration group, the increase in the avoidance response score was suppressed as compared with that in the vincristine administration group (filled circles with a solid line).

Further, it was found that, in the vincristine+*Lentinus edodes* mycelium extract administration group (open squares with a dash line), suppression of the decrease in the pain threshold was continued even after finishing the administration of the *Lentinus edodes* mycelium extract (on Day 15 or later).

(3) Cold Plate Test

In the present test, the mice were divided into three groups by a difference in test objects. As in Example 1, male Balb/c mice of 6 to 7 weeks old were used. The mice were divided into a total of three groups, a control group, a vincristine administration group, and a vincristine and *Lentinus edodes* mycelium extract administration group (vincristine+*Lentinus edodes* mycelium extract administration group).

Vincristine was administered to each mouse once a day at a dose of 0.2 mg/kg. Further, the *Lentinus edodes* mycelium extract was administered to each mouse once a day at a dose of 2 g/kg.

Figure 6:
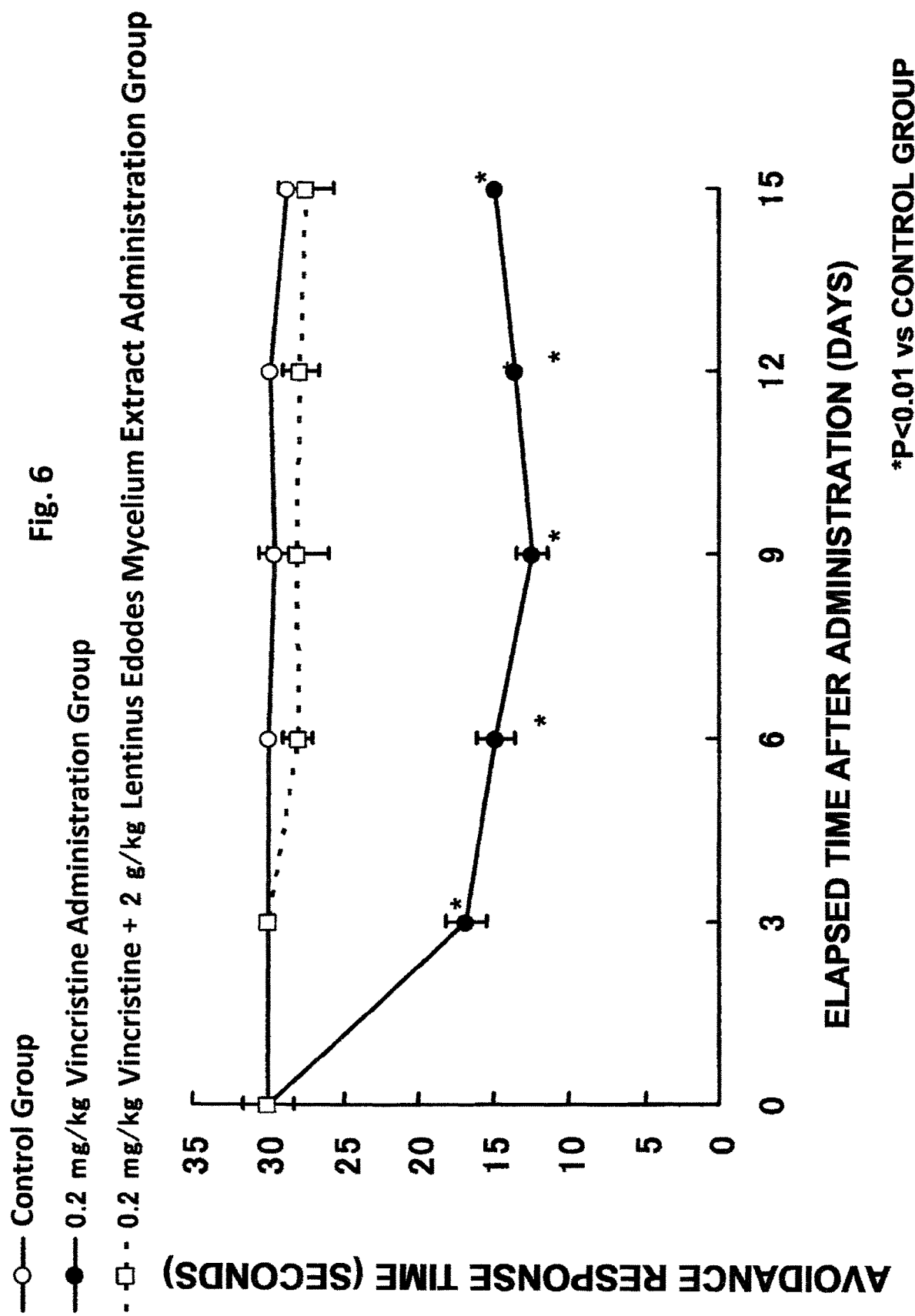
FIG. 6 is a diagram illustrating a result of the cold plate test in which the composition for ameliorating peripheral sensory neuropathy according to the present invention is coadministered with vincristine.

Evaluation was performed in the same manner as in the test with oxaliplatin in Example 1. The result is shown in FIG. 6. Referring to FIG. 6, the horizontal axis indicates the elapsed time after administration (days) and the vertical axis indicates the avoidance response time (seconds). Open circles with a solid line represent the control group. Filled circles with a solid line represent the group in which only vincristine was administered. Open squares with a dash line represent the group in which vincristine and the *Lentinus edodes* mycelium extract were administered at the same time (vincristine+*Lentinus edodes* mycelium extract administration group). When the difference with the control group was determined to be significant using a significance level of 5%, the data were marked by "*".

Referring to FIG. 6, on Day 3 in the test, the latency to the cold stimulation of the cold plate was significantly reduced in the vincristine administration group (filled circles with a solid line). This suggests that the peripheral sensory neuropathy was developed by the administration of vincristine. On the other hand, the vincristine+*Lentinus edodes* mycelium extract administration group (open squares with a dash line) showed the latency of about the same level as that in the control group (open circles with a solid line). The decrease in the latency was suppressed in the vincristine+*Lentinus edodes* mycelium extract administration group as compared with that in the group in which only vincristine was administered (filled circles with a solid line).

(Example 4) <Effect on Peripheral Sensory Neuropathy Induced by Bortezomib in Mice>

The effect of the *Lentinus edodes* mycelium extract of the present invention on hyperesthesia such as allodynia to mechanical stimulation and paresthesia to cold stimulation induced by administration of bortezomib as the anticancer drug was examined. It is known that bortezomib inhibits proteasome and thus induces apoptosis by inhibiting degradation of an apoptosis inducing factor. The *Lentinus edodes* mycelium extract of the present invention was orally administered to mice, and the tests (the cold plate test and the von Frey test) were performed in the same manner as in Example 1.

(1) Administration of Test Object

In the present test, the mice were divided into three groups by a difference in test objects. As in Example 1, male Balb/c mice of 6 to 7 weeks old were used. The mice were divided into a total of three groups, a control group, a bortezomib administration group, and a bortezomib and *Lentinus edodes* mycelium extract administration group (bortezomib+*Lentinus edodes* mycelium extract administration group).

Bortezomib was administered to each mouse once a day at a dose of 1 mg/kg. Further, the *Lentinus edodes* mycelium extract was administered to each mouse once a day at a dose of 2 g/kg.

Further, the number of times of administration was set to once a week (on Day 0, Day 7, and Day 14) for bortezomib and daily (from Day 0 to Day 15) for the *Lentinus edodes* mycelium extract in both the von Frey test and the cold plate test below.

(2) Von Frey Test

Figure 7:
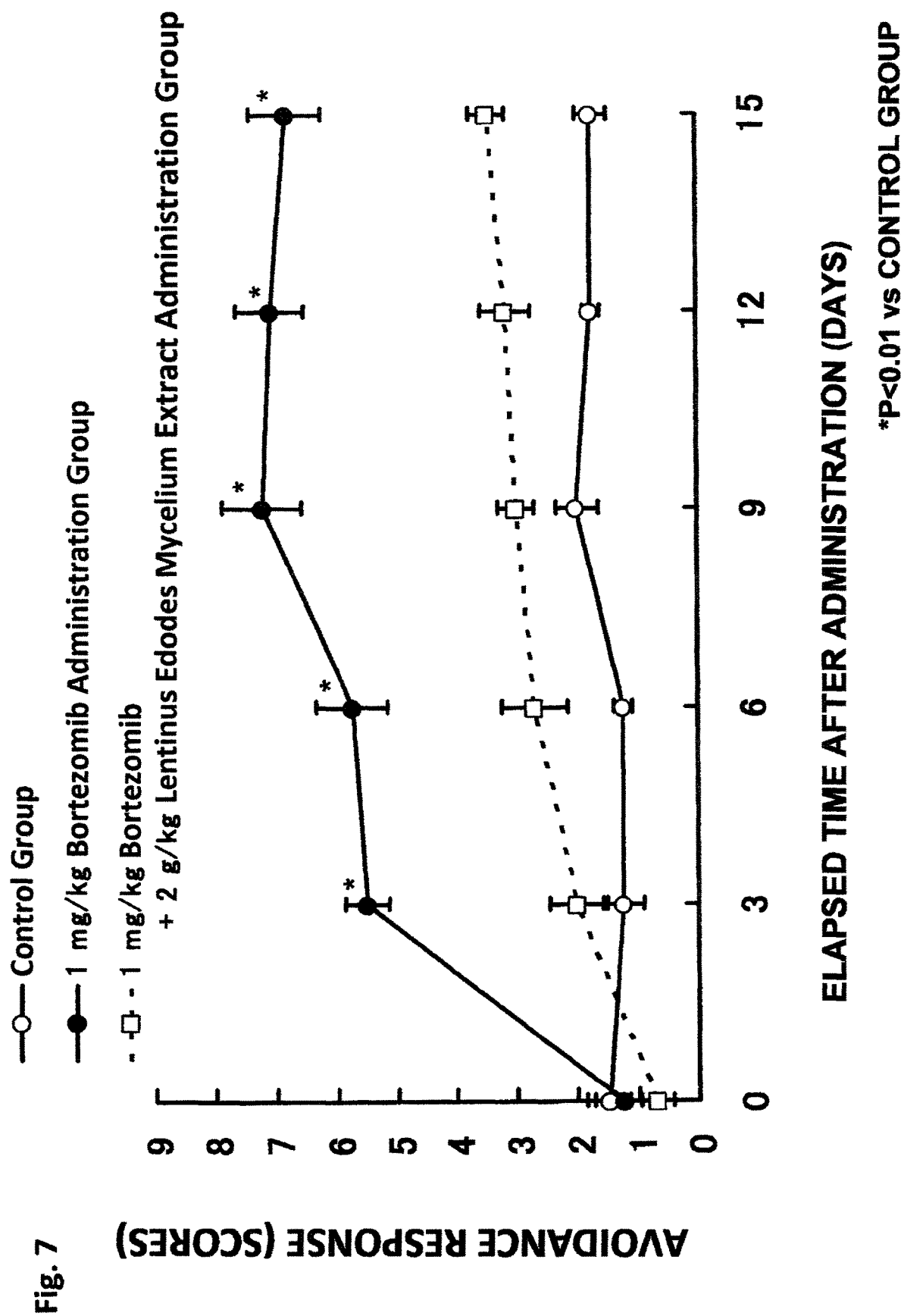
FIG. 7 is a diagram illustrating a result of the von Frey test in which the composition for ameliorating peripheral sensory neuropathy according to the present invention is coadministered with bortezomib.

Evaluation was performed in the same manner as in the test with oxaliplatin in Example 1. The result is shown in FIG. 7. Referring to FIG. 7, the horizontal axis indicates an elapsed time after administration (days) and the vertical axis indicates the avoidance response (scores). Open circles with a solid line represent the control group. Filled circles with a solid line represent the group in which only bortezomib was administered. Open squares with a dash line represent the group in which bortezomib and the *Lentinus edodes* mycelium extract were administered at the same time (bortezomib+*Lentinus edodes* mycelium extract administration group). When the difference with the control group was determined to be significant using a significance level of 5%, the data were marked by "*".

In the bortezomib administration group (filled circles with a solid line), the avoidance response score significantly increased three days after the administration as compared with the control group (open circles with a solid line). This suggests that the peripheral sensory neuropathy was developed by the administration of bortezomib. The bortezomib+*Lentinus edodes* mycelium extract administration group (open squares with a dash line) showed the avoidance response score of the same level as that in the control group. In the bortezomib+*Lentinus edodes* mycelium extract administration group, the increase in the avoidance response score was suppressed as compared with that in the bortezomib administration group (filled circles with a solid line).

Further, it was found that, in the bortezomib+*Lentinus edodes* mycelium extract administration group (open squares with a dash line), suppression of the decrease in the pain threshold was continued even after finishing the administration of the *Lentinus edodes* mycelium extract (on Day 16 or later).

(3) Cold Plate Test

In the present test, the mice were divided into three groups by a difference in test objects. As in Example 1, male Balb/c mice of 6 to 7 weeks old were used. The mice were divided into a total of three groups, a control group, a bortezomib administration group, and a bortezomib and *Lentinus edodes* mycelium extract administration group (bortezomib+*Lentinus edodes* mycelium extract administration group).

Bortezomib was administered to each mouse once a day at a dose of 1 mg/kg. Further, the *Lentinus edodes* mycelium extract was administered to each mouse once a day at a dose of 2 g/kg.

Figure 8:
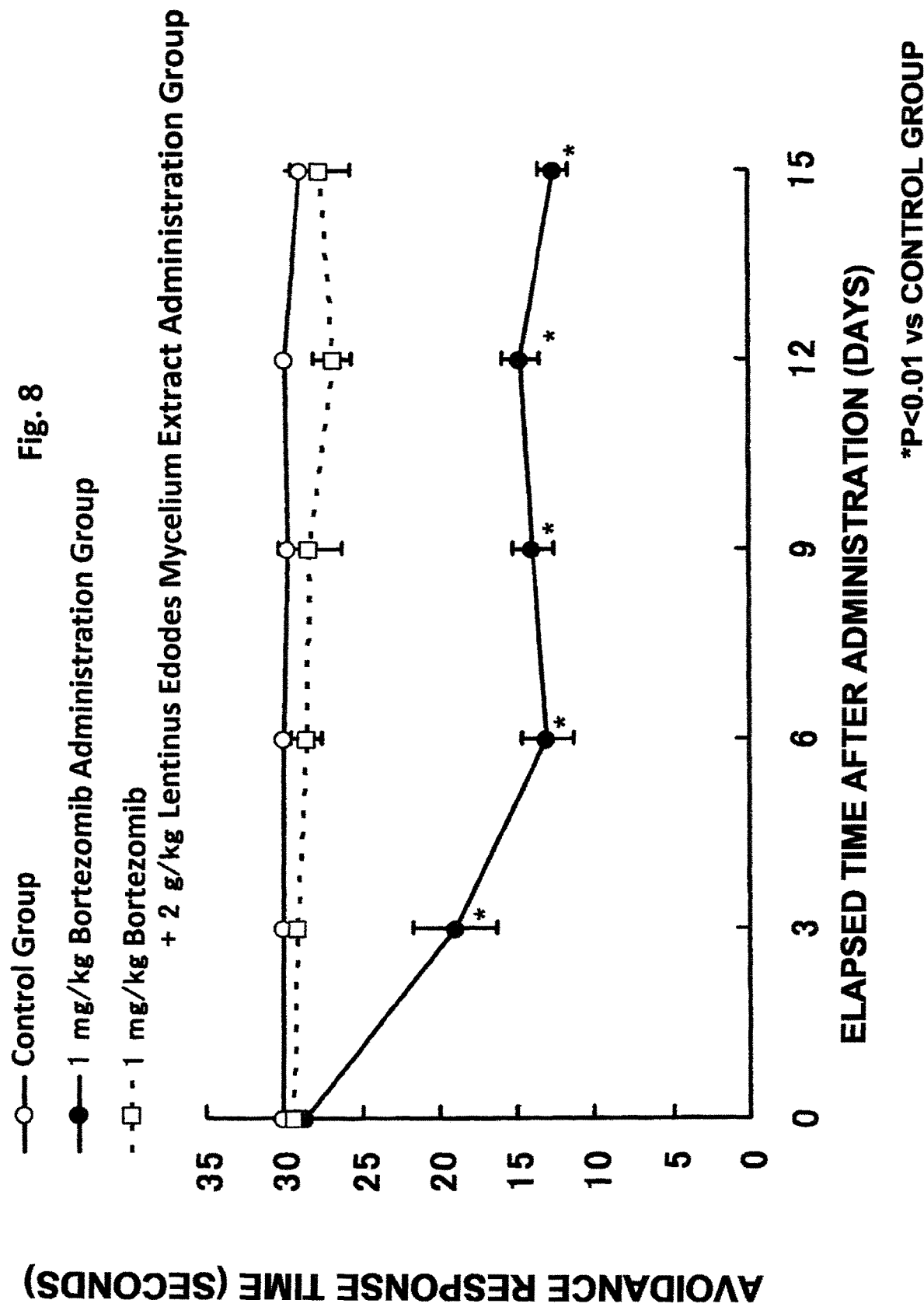
FIG. 8 is a diagram illustrating a result of the cold plate test in which the composition for ameliorating peripheral sensory neuropathy according to the present invention is coadministered with bortezomib.

Evaluation was performed in the same manner as in the test with oxaliplatin in Example 1. The result is shown in FIG. 8. Referring to FIG. 8, the horizontal axis indicates the elapsed time after administration (days) and the vertical axis indicates the avoidance response time (seconds). Open circles with a solid line represent the control group. Filled circles with a solid line represent the group in which only bortezomib was administered. Open squares with a dash line represent the group in which bortezomib and the *Lentinus edodes* mycelium extract were administered at the same time (bortezomib+*Lentinus edodes* mycelium extract administration groups). When the difference with the control group was determined to be significant using a significance level of 5%, the data were marked by "*".

Referring to FIG. 8, on Day 3 in the test, the latency to the cold stimulation of the cold plate was significantly reduced in the bortezomib administration group (filled circles with a solid line). This suggests that the peripheral sensory neuropathy was developed by the administration of bortezomib. On the other hand, the bortezomib+*Lentinus edodes* mycelium extract administration group (open squares with a dash line) showed the latency of about the same level as that in the control group (open circles with a solid line). The decrease in the latency was suppressed in the bortezomib+*Lentinus edodes* mycelium extract administration group as compared with that in the group in which only bortezomib was administered (filled circles with a solid line).

Examples 1 to 4 showed that coadministration of the *Lentinus edodes* mycelium extract according to the present invention could exhibit the effect of inhibiting the onset of the peripheral sensory neuropathy induced by four representative anticancer drugs. Thus, the composition for ameliorating peripheral sensory neuropathy including the *Lentinus edodes* mycelium extract according to the present invention can be considered as a composition for preventing peripheral sensory neuropathy (a medical composition for preventing peripheral sensory neuropathy). However, in the actual practice of the cancer treatment, there is a very high demand for a composition for treating peripheral sensory neuropathy that alleviates the symptom of the side effect (the peripheral sensory neuropathy) once developed.

The *Lentinus edodes* mycelium extract according to the present invention can inhibit (prevent) the onset of the peripheral sensory neuropathy when coadministered with the anticancer drug. However, the *Lentinus edodes* mycelium extract according to the present invention can also serve as a composition for treating peripheral sensory neuropathy (a medical composition for treating peripheral sensory neuropathy) that alleviates the peripheral sensory neuropathy once developed. Examples thereof will be described below.

(Example 5) <Treatment Effect on Peripheral Sensory Neuropathy Induced by Oxaliplatin in Mice>

The treatment effect of the *Lentinus edodes* mycelium extract of the present invention on hyperesthesia such as allodynia to mechanical stimulation and paresthesia to cold stimulation induced by administration of oxaliplatin as the anticancer drug was examined. The anticancer drug, oxaliplatin, was administered to mice to induce the peripheral sensory neuropathy, and then, the *Lentinus edodes* mycelium extract of the present invention was orally administered to the mice to perform the same tests (the cold plate test and the von Frey test) as those in Example 1.

(1) Administration of Test Object

In the present test, the mice were divided into six groups by a difference in test objects. As in Example 1, male Balb/c mice of 6 to 7 weeks old were used. The mice were divided into a total of six groups, a control group, an oxaliplatin administration group, two different oxaliplatin and *Lentinus edodes* mycelium extract administration groups (oxaliplatin+*Lentinus edodes* mycelium extract administration groups), and two different oxaliplatin and duloxetine administration groups (oxaliplatin+duloxetine administration groups).

Oxaliplatin was administered to each mouse once a day at a dose of 6 mg/kg. Further, the *Lentinus edodes* mycelium extract was administered to each mouse once a day at a dose of 2 g/kg three days or six days after the administration of oxaliplatin. These groups are referred to as "*Lentinus edodes* mycelium 3-day delayed administration group" and "*Lentinus edodes* mycelium 6-day delayed administration group", respectively.

Further, groups in which duloxetine was administered after the administration of oxaliplatin were prepared for comparison. Duloxetine, which is an antidepressant, is applied to a pain accompanied by a diabetic neuropathy and a pain accompanied by fibromyalgia. Duloxetine is sometimes used for the peripheral sensory neuropathy induced by the anticancer drug with a non-opioid or opioid analgesic.

Duloxetine was also administered once a day at a dose of 30 mg/kg three days or six days after the administration of oxaliplatin. These groups are referred to as "duloxetine 3-day delayed administration group" and "duloxetine 6-day delayed administration group", respectively.

Further, the number of times of administration was set to once a week (on Day 0, Day 7, Day 14, and Day 21) for oxaliplatin and daily from the administration start date (from Day 3 or Day 6 to Day 23) for the *Lentinus edodes* mycelium extract and duloxetine in both the von Frey test and the cold plate test below.

(2) Von Frey Test

Figure 9:
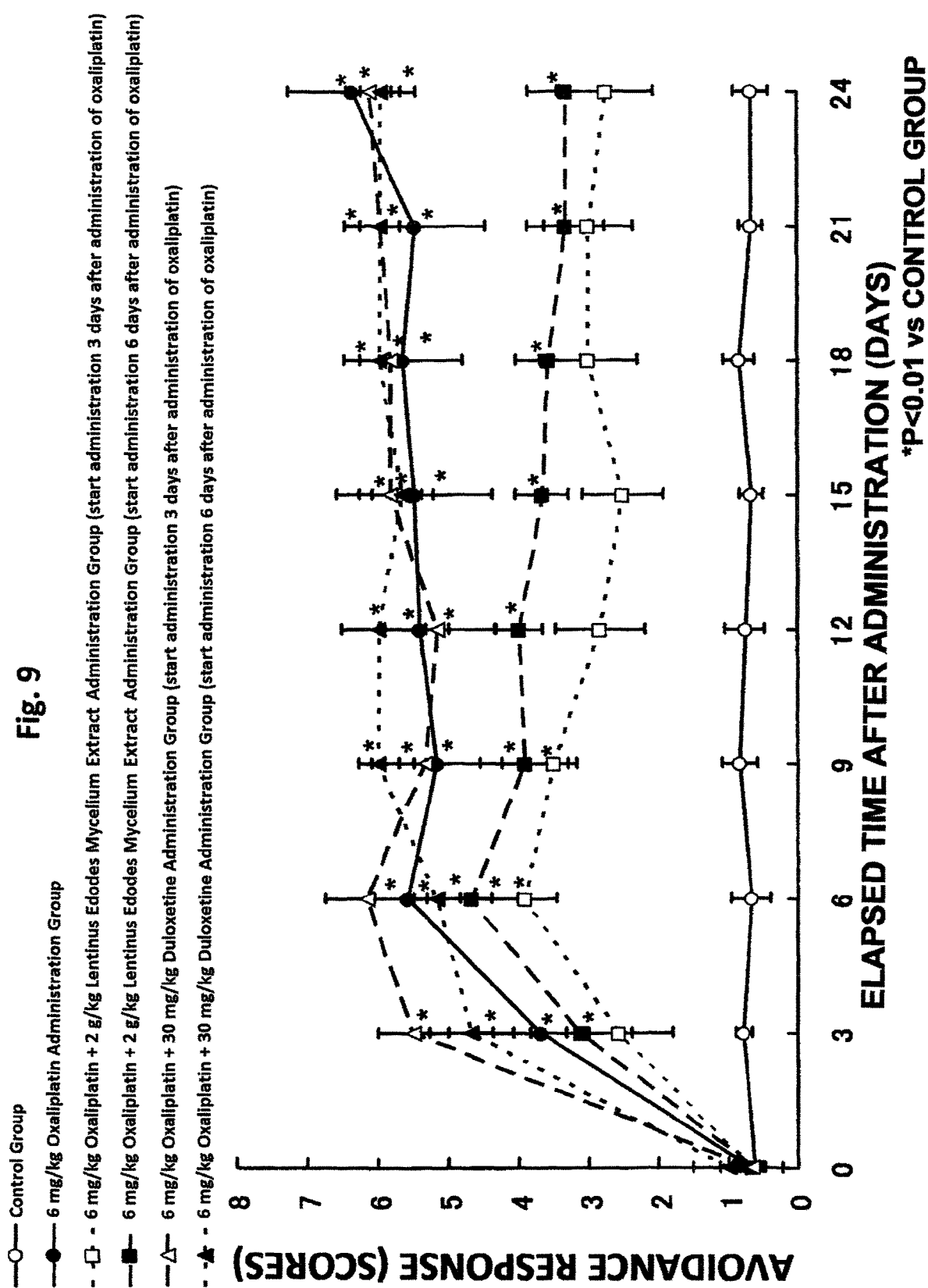
FIG. 9 is a diagram illustrating a result of the von Frey test in which the composition for ameliorating peripheral sensory neuropathy according to the present invention is administered after administration of oxaliplatin.

Evaluation was performed in the same manner as in the test with oxaliplatin in Example 1. The result is shown in FIG. 9. Referring to FIG. 9, the horizontal axis indicates the elapsed time after administration (days) and the vertical axis indicates the avoidance response (scores). Open circles with a solid line represent the control group. Filled circles with a solid line represent the group in which only oxaliplatin was administered. Open squares with a dash line and filled squares with a dash line represent the groups in which the *Lentinus edodes* mycelium extract was administered after the administration of oxaliplatin ("*Lentinus edodes* mycelium extract 3-day delayed administration group" and "*Lentinus edodes* mycelium extract 6-day delayed administration group", respectively).

Further, open triangles with a dash line and filled triangles with a dash line represent the groups in which duloxetine was administered after the administration of oxaliplatin ("duloxetine 3-day delayed administration group" and "duloxetine 6-day delayed administration group", respectively). When the difference with the control group was determined to be significant using a significance level of 5%, the data were marked by "*".

The avoidance response score significantly increased in the oxaliplatin administration group (filled circles with a solid line) as compared with the control group (open circles with a solid line). As also shown in FIG. 1, this suggests that the peripheral sensory neuropathy was developed by the administration of oxaliplatin. The *Lentinus edodes* mycelium extract 3-day delayed administration group (open squares with a dash line) had the lower avoidance score than the oxaliplatin administration group (filled circles with a solid line) after the administration. The *Lentinus edodes* mycelium extract 3-day delayed administration group could maintain the clearly lower value than that in the oxaliplatin administration group (filled circles with a solid line) on Day 6 or later, if not as low as the control group (open circles with a solid line).

Further, the *Lentinus edodes* mycelium extract 6-day delayed administration group (filled squares with a dash line) also maintained the clearly lower score than that in the oxaliplatin administration group (filled circles with a solid line) on Day 9 or later. That is, the *Lentinus edodes* mycelium extract administered after the onset of the peripheral sensory neuropathy is still effective for inhibiting the symptom.

On the other hand, in the duloxetine 3-day delayed administration group (open triangles with a dash line), the avoidance score never became lower than that in the oxaliplatin administration group (filled circles with a solid line) after the administration. The duloxetine 3-day delayed administration group (open triangles with a dash line) had almost the same score as that in the oxaliplatin administration group (filled circles with a solid line). Further, the duloxetine 6-day delayed administration group (filled triangles with a dash line) showed the same tendency as that in the duloxetine 3-day delayed administration group (open triangles with a dash line). That is, this suggests that duloxetine does not significantly contribute to the inhibition of the peripheral sensory neuropathy.

It was found that the suppression of the decrease in the pain threshold was maintained even after finishing the administration of the *Lentinus edodes* mycelium extract (Day 23 or later) in the *Lentinus edodes* mycelium extract 3-day delayed administration group (open squares with a dash line) and the *Lentinus edodes* mycelium extract 6-day delayed administration group.

(3) Cold Plate Test

In the present test, the mice were divided into six groups by a difference in test objects. As in Example 1, male Balb/c mice of 6 to 7 weeks old were used. The mice were divided into a total of six groups, a control group, an oxaliplatin administration group, two different oxaliplatin and *Lentinus edodes* mycelium extract administration groups (oxaliplatin+*Lentinus edodes* mycelium extract administration groups), and two different oxaliplatin and duloxetine administration groups (oxaliplatin+duloxetine administration groups).

Oxaliplatin was administered to each mouse once a day at a dose of 6 mg/kg. Further, the *Lentinus edodes* mycelium extract was administered to each mouse once a day at a dose of 2 g/kg three days or six days after the administration of oxaliplatin. These groups are referred to as "*Lentinus edodes* mycelium extract 3-day delayed administration group" and "*Lentinus edodes* mycelium extract 6-day delayed administration group", respectively.

Further, groups in which duloxetine was administered after the administration of oxaliplatin were prepared for comparison. Duloxetine was also administered once a day at a dose of 30 mg/kg three days or six days after the administration of oxaliplatin. These groups are referred to as "duloxetine 3-day delayed administration group" and "duloxetine 6-day delayed administration group", respectively.

Figure 10:
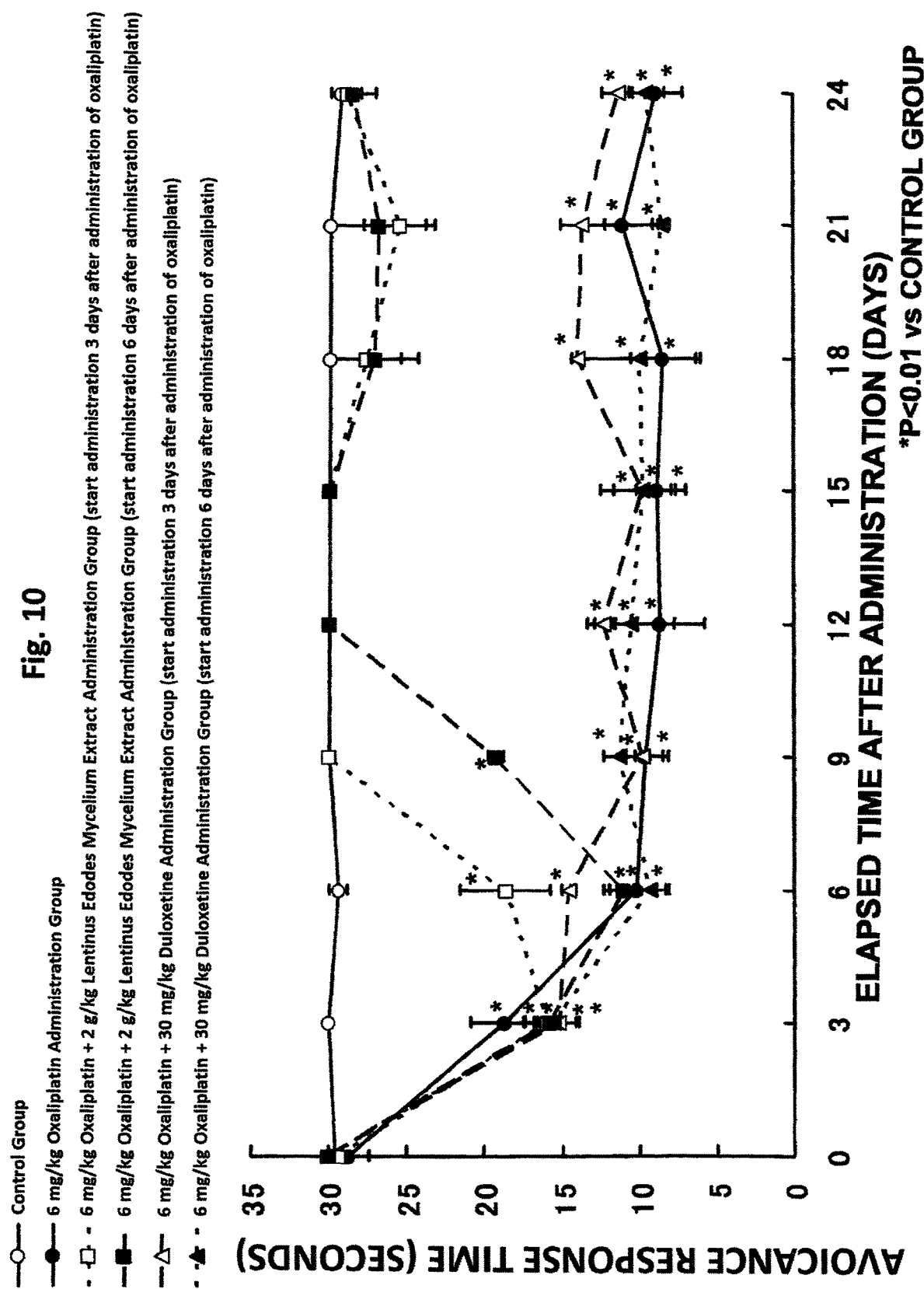
FIG. 10 is a diagram illustrating a result of the cold plate test in which the composition for ameliorating peripheral sensory neuropathy according to the present invention is administered after administration of oxaliplatin.

Evaluation was performed in the same manner as in the test with oxaliplatin in Example 1. The result is shown in FIG. 10. Referring to FIG. 10, the horizontal axis indicates the elapsed time after administration (days) and the vertical axis indicates the avoidance response time (seconds). Open circles with a solid line represent the control group. Filled circles with a solid line represent the group in which only oxaliplatin was administered. Open squares with a dash line and filled squares with a dash line represent the groups in which the *Lentinus edodes* mycelium extract was administered after the administration of oxaliplatin ("*Lentinus edodes* mycelium extract 3-day delayed administration group" and "*Lentinus edodes* mycelium extract 6-day delayed administration group", respectively).

Further, open triangles with a dash line and filled triangles with a dash line represent the groups in which duloxetine was administered after the administration of oxaliplatin ("duloxetine 3-day delayed administration group" and "duloxetine 6-day delayed administration group", respectively). When the difference with the control group was determined to be significant using a significance level of 5%, the data were marked by "*".

Referring to FIG. 10, on Day 3 in the test, the latency to the cold stimulation of the cold plate was significantly reduced in the oxaliplatin administration group (filled circles with a solid line). This suggests that the peripheral sensory neuropathy was developed by oxaliplatin as seen in the von Frey test. The latency in the *Lentinus edodes* mycelium extract 3-day delayed administration group (open squares with a dash line) became clearly longer than that in the oxaliplatin administration group (filled circles with a solid line) after the administration. The latency in the *Lentinus edodes* mycelium extract 3-day delayed administration group was recovered to the same level as that in the control (open circles with a solid line) on Day 9 or later. Further, the latency in the *Lentinus edodes* mycelium extract 6-day delayed administration group (filled squares with a dash line) also became longer after the administration and was recovered to the same level as that in the control (open circles with a solid line) on Day 12.

On the other hand, the latency in the duloxetine 3-day delayed administration group (open triangles with a dash line) never became longer than that in the oxaliplatin administration group (filled circles with a solid line) after the administration. The latency in the duloxetine 3-day delayed administration group was almost the same as that in the oxaliplatin administration group (filled circles with a solid line). Further, the duloxetine 6-day delayed administration group (filled triangles with a dash line) showed the same tendency as that in the duloxetine 3-day delayed administration group (open triangles with a dash line). That is, this suggests that duloxetine does not significantly contribute to the inhibition of the peripheral sensory neuropathy (the cold hypersensitivity).

As described above, when used with the anticancer drug (oxaliplatin), the *Lentinus edodes* mycelium extract according to the present invention can not only inhibit the peripheral sensory neuropathy, but also serve as the composition for treating peripheral sensory neuropathy (the medical composition for treating peripheral sensory neuropathy) that alleviates the symptom of the peripheral sensory neuropathy once developed.

(Example 6) <Treatment Effect on Peripheral Sensory Neuropathy Induced by Paclitaxel in Mice>

The treatment effect of the *Lentinus edodes* mycelium extract of the present invention on hyperesthesia such as allodynia to mechanical stimulation and paresthesia to cold stimulation induced by administration of paclitaxel as the anticancer drug was examined. The anticancer drug, paclitaxel, was administered to mice to induce the peripheral sensory neuropathy, and then, the *Lentinus edodes* mycelium extract of the present invention was orally administered to the mice to perform the same tests (the cold plate test and the von Frey test) as those in Example 1.

(1) Administration of Test Object

In the present test, the mice were divided into six groups by a difference in test objects. As in Example 1, male Balb/c mice of 6 to 7 weeks old were used. The mice were divided into a total of six groups, a control group, a paclitaxel administration group, two different paclitaxel and *Lentinus edodes* mycelium extract administration groups (paclitaxel+ *Lentinus edodes* mycelium extract administration groups), and two different paclitaxel and duloxetine administration groups (paclitaxel+duloxetine administration groups).

Paclitaxel was administered to each mouse once a day at a dose of 6 mg/kg. Further, the *Lentinus edodes* mycelium extract was administered to each mouse once a day at a dose of 2 g/kg three days or six days after the administration of paclitaxel. These groups are referred to as "*Lentinus edodes* mycelium extract 3-day delayed administration group" and "*Lentinus edodes* mycelium extract 6-day delayed administration group", respectively. Further, groups in which duloxetine was administered after the administration of paclitaxel were prepared for comparison.

Duloxetine was also administered once a day at a dose of 30 mg/kg three days or six days after the administration of paclitaxel. These groups are referred to as "duloxetine 3-day delayed administration group" and "duloxetine 6-day delayed administration group", respectively.

Further, the number of times of administration was set to once a week (on Day 0, Day 7, Day 14, and Day 21) for paclitaxel and daily from the administration start date (from Day 3 or Day 6 to Day 23) for the *Lentinus edodes* mycelium extract and duloxetine in both the von Frey test and the cold plate test below.

(2) Von Frey Test

Figure 11:
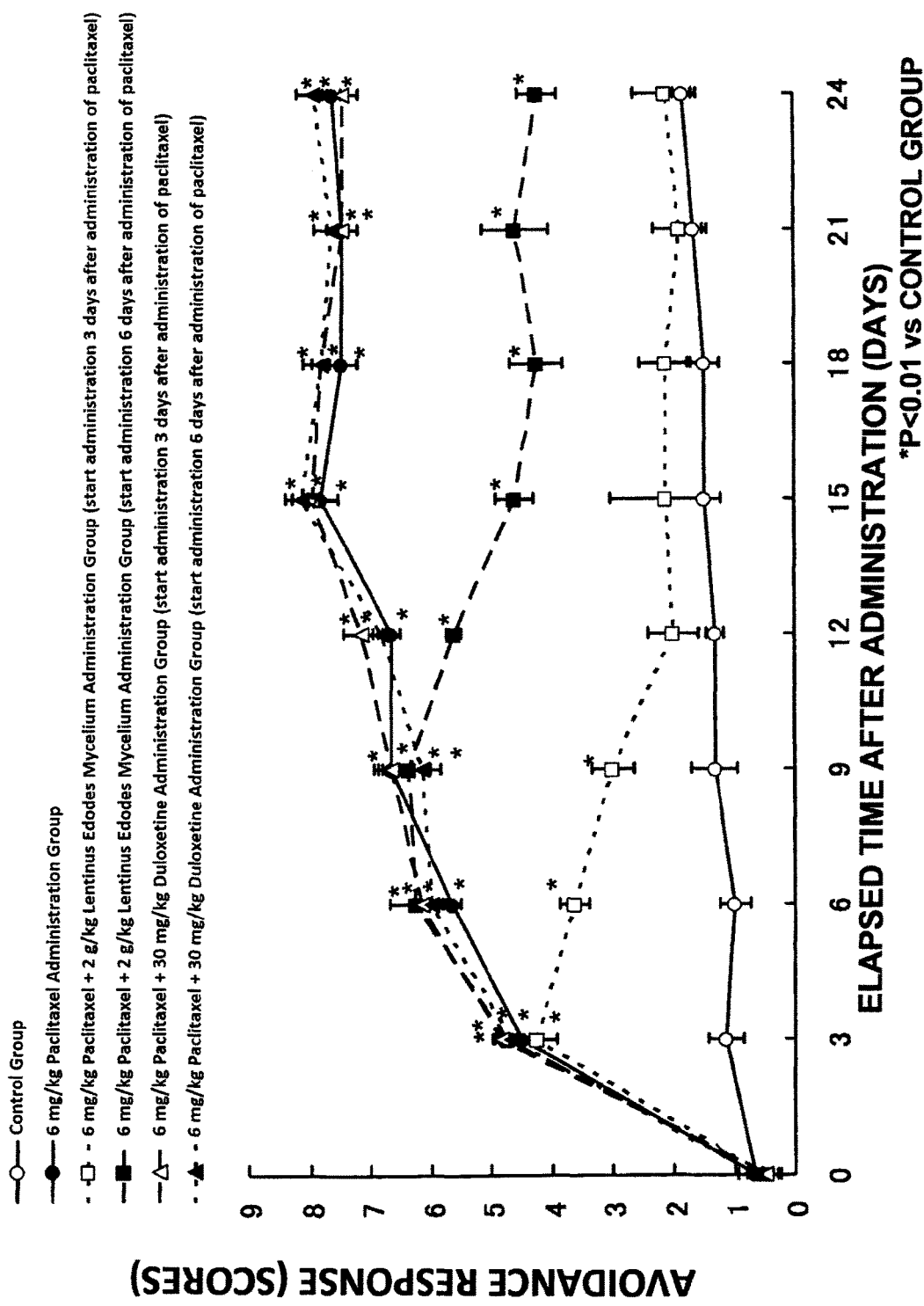
FIG. 11 is a diagram illustrating a result of the von Frey test in which the composition for ameliorating peripheral sensory neuropathy according to the present invention is administered after administration of paclitaxel.

Evaluation was performed in the same manner as in the test with oxaliplatin in Example 1. The result is shown in FIG. 11. Referring to FIG. 11, the horizontal axis indicates the elapsed time after administration (days) and the vertical axis indicates the avoidance response (scores). Open circles with a solid line represent the control group. Filled circles with a solid line represent the group in which only paclitaxel was administered. Open squares with a dash line and filled squares with a dash line represent the groups in which the *Lentinus edodes* mycelium extract was administered after the administration of paclitaxel ("*Lentinus edodes* mycelium extract 3-day delayed administration group" and "*Lentinus edodes* mycelium extract 6-day delayed administration group", respectively).

Further, open triangles with a dash line and filled triangles with a dash line represent the groups in which duloxetine was administered after the administration of paclitaxel ("duloxetine 3-day delayed administration group" and "duloxetine 6-day delayed administration group", respectively). When the difference with the control group was determined to be significant using a significance level of 5%, the data were marked by "*".

The avoidance response score significantly increased in the paclitaxel administration group (filled circles with a solid line) three day after the administration as compared with the control group (open circles with a solid line). This suggests that the peripheral sensory neuropathy was developed by the administration of paclitaxel. The *Lentinus edodes* mycelium extract 3-day delayed administration group (open squares with a dash line) had the lower avoidance score than that in the paclitaxel administration group (filled circles with a solid line) after the administration. The avoidance score in the *Lentinus edodes* mycelium extract 3-day delayed administration group was recovered to the same level as that in the control (open circles with a solid line) on Day 12. Further, the *Lentinus edodes* mycelium extract 6-day delayed administration group (filled squares with a dash line) also maintained the clearly lower score than that in the paclitaxel administration group (filled circles with a solid line) on Day 12 or later. That is, the *Lentinus edodes* mycelium extract administered after the onset of the peripheral sensory neuropathy is still effective for inhibiting the symptom.

On the other hand, in the duloxetine 3-day delayed administration group (open triangles with a dash line), the avoidance score never became lower than that in the paclitaxel administration group (filled circles with a solid line) after the administration. The duloxetine 3-day delayed administration group (open triangles with a dash line) had almost the same avoidance score as that in the paclitaxel administration group (filled circles with a solid line). Further, the duloxetine 6-day delayed administration group (filled triangles with a dash line) showed the same tendency as that in the duloxetine 3-day delayed administration group (open triangles with a dash line). That is, this suggests that duloxetine does not significantly contribute to the inhibition of the peripheral sensory neuropathy.

It was found that the suppression of the decrease in the pain threshold was maintained even after finishing the administration of the *Lentinus edodes* mycelium extract (Day 23 or later) in the *Lentinus edodes* mycelium extract 3-day delayed administration group (open squares with a dash line) and the *Lentinus edodes* mycelium extract 6-day delayed administration group.

(3) Cold Plate Test

In the present test, the mice were divided into six groups by a difference in test objects. As in Example 1, male Balb/c mice of 6 to 7 weeks old were used. The mice were divided into a total of six groups, a control group, a paclitaxel administration group, two different paclitaxel and *Lentinus edodes* mycelium extract administration groups (paclitaxel+ *Lentinus edodes* mycelium extract administration groups), and two different paclitaxel and duloxetine administration groups (paclitaxel+duloxetine administration groups).

Paclitaxel was administered to each mouse once a day at a dose of 6 mg/kg. Further, the *Lentinus edodes* mycelium extract was administered to each mouse once a day at a dose of 2 g/kg three days or six days after the administration of paclitaxel. These groups are referred to as "*Lentinus edodes* mycelium extract 3-day delayed administration group" and "*Lentinus edodes* mycelium extract 6-day delayed administration group", respectively.

Further, groups in which duloxetine was administered after the administration of paclitaxel were prepared for comparison. Duloxetine was also administered once a day at a dose of 30 mg/kg three days or six days after the administration of paclitaxel. These groups are referred to as "duloxetine 3-day delayed administration group" and "duloxetine 6-day delayed administration group", respectively.

Figure 12:
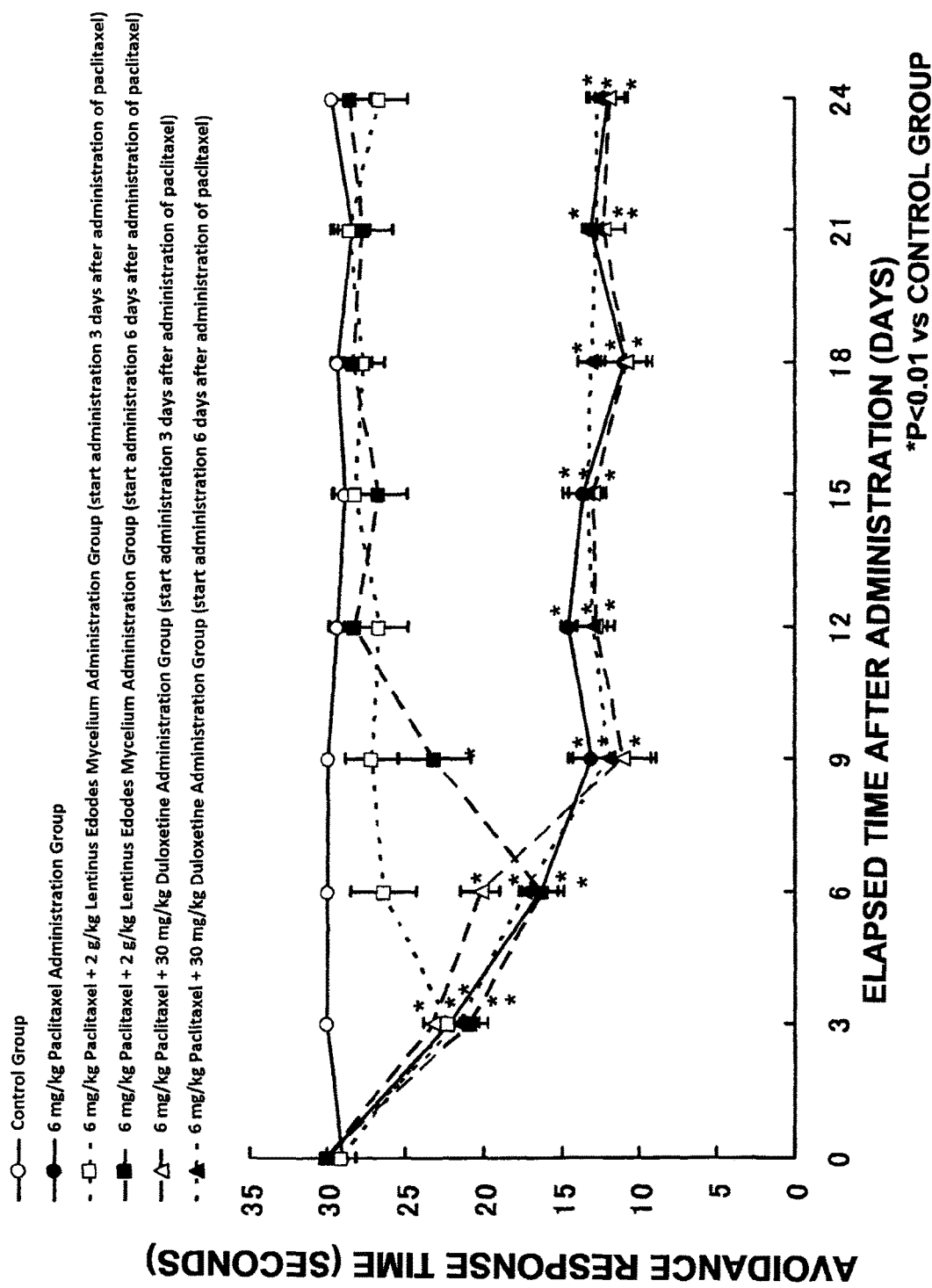
FIG. 12 is a diagram illustrating a result of the cold plate test in which the composition for ameliorating peripheral sensory neuropathy according to the present invention is administered after administration of paclitaxel.

Evaluation was performed in the same manner as in the test with oxaliplatin in Example 1. The result is shown in FIG. 12. Referring to FIG. 12, the horizontal axis indicates the elapsed time after administration (days) and the vertical axis indicates the avoidance response time (seconds). Open circles with a solid line represent the control group. Filled circles with a solid line represent the group in which only paclitaxel was administered. Open squares with a dash line and filled squares with a dash line represent the groups in which the *Lentinus edodes* mycelium extract was administered after the administration of paclitaxel ("*Lentinus edodes* mycelium extract 3-day delayed administration group" and "*Lentinus edodes* mycelium extract 6-day delayed administration group", respectively).

Further, open triangles with a dash line and filled triangles with a dash line represent the groups in which duloxetine was administered after the administration of paclitaxel ("duloxetine 3-day delayed administration group" and "duloxetine 6-day delayed administration group", respectively). When the difference with the control group was determined to be significant using a significance level of 5%, the data were marked by "*".

Referring to FIG. 12, on Day 3 in the test, the latency to the cold stimulation of the cold plate was significantly reduced in the paclitaxel administration group (filled circles with a solid line). This suggests that the peripheral sensory neuropathy was developed by paclitaxel as seen in the von Frey test. The latency in the *Lentinus edodes* mycelium extract 3-day delayed administration group (open squares with a dash line) became clearly longer than that in the paclitaxel administration group (filled circles with a solid line) after the administration. The latency in the *Lentinus edodes* mycelium extract 3-day delayed administration group (open squares with a dash line) was recovered to the same level as that in the control (open circles with a solid line) on Day 15 or later. Further, the latency in the *Lentinus edodes* mycelium extract 6-day delayed administration group (filled squares with a dash line) also became longer after the administration. The latency in the *Lentinus edodes* mycelium extract 6-day delayed administration group (filled squares with a dash line) was recovered to the same level as that in the control (open circles with a solid line) on Day 18 or later.

On the other hand, the latency in the duloxetine 3-day delayed administration group (open triangles with a dash line) never became longer than that in the paclitaxel administration group (filled circles with a solid line) after the administration. The latency in the duloxetine 3-day delayed administration group was almost the same as that in the paclitaxel administration group (filled circles with a solid line). Further, the duloxetine 6-day delayed administration group (filled triangles with a dash line) showed the same tendency as that in the duloxetine 3-day delayed administration group (open triangles with a dash line). That is, this suggests that duloxetine does not significantly contribute to the inhibition of the peripheral sensory neuropathy (the cold hypersensitivity).

As described above, when used with the anticancer drug (paclitaxel), the *Lentinus edodes* mycelium extract according to the present invention can not only inhibit the peripheral sensory neuropathy, but also serve as the composition for treating peripheral sensory neuropathy (the medical composition for treating peripheral sensory neuropathy) that alleviates the symptom of the peripheral sensory neuropathy once developed.

(Example 7) <Treatment Effect on Peripheral Sensory Neuropathy Induced by Vincristine in Mice>

The treatment effect of the *Lentinus edodes* mycelium extract of the present invention on hyperesthesia such as allodynia to mechanical stimulation and paresthesia to cold stimulation induced by administration of vincristine as the anticancer drug was examined. The anticancer drug, vincristine, was administered to mice to induce the peripheral sensory neuropathy, and then, the *Lentinus edodes* mycelium extract of the present invention was orally administered to the mice to perform the same tests (the cold plate test and the von Frey test) as those in Example 1.

(1) Administration of Test Object

In the present test, the mice were divided into six groups by a difference in test objects. As in Example 1, male Balb/c mice of 6 to 7 weeks old were used. The mice were divided into a total of six groups, a control group, a vincristine administration group, two different vincristine and *Lentinus edodes* mycelium extract administration groups (vincristine+*Lentinus edodes* mycelium extract administration groups), and two different vincristine and duloxetine administration groups (vincristine+duloxetine administration groups).

Vincristine was administered to each mouse once a day at a dose of 0.2 mg/kg. Further, the *Lentinus edodes* mycelium extract was administered to each mouse once a day at a dose of 2 g/kg three days or six days after the administration of vincristine. These groups are referred to as "*Lentinus edodes* mycelium extract 3-day delayed administration group" and "*Lentinus edodes* mycelium extract 6-day delayed administration group", respectively. Further, groups in which duloxetine was administered after the administration of vincristine were prepared for comparison.

Duloxetine was also administered once a day at a dose of 30 mg/kg three days or six days after the administration of vincristine. These groups are referred to as "duloxetine 3-day delayed administration group" and "duloxetine 6-day delayed administration group", respectively.

Further, the number of times of administration was set to once a week (on Day 0, Day 7, Day 14, and Day 21) for vincristine and daily from the administration start date (from Day 3 or Day 6 to Day 23) for the *Lentinus edodes* mycelium extract and duloxetine in both the von Frey test and the cold plate test below.

(2) Von Frey Test

Figure 13:
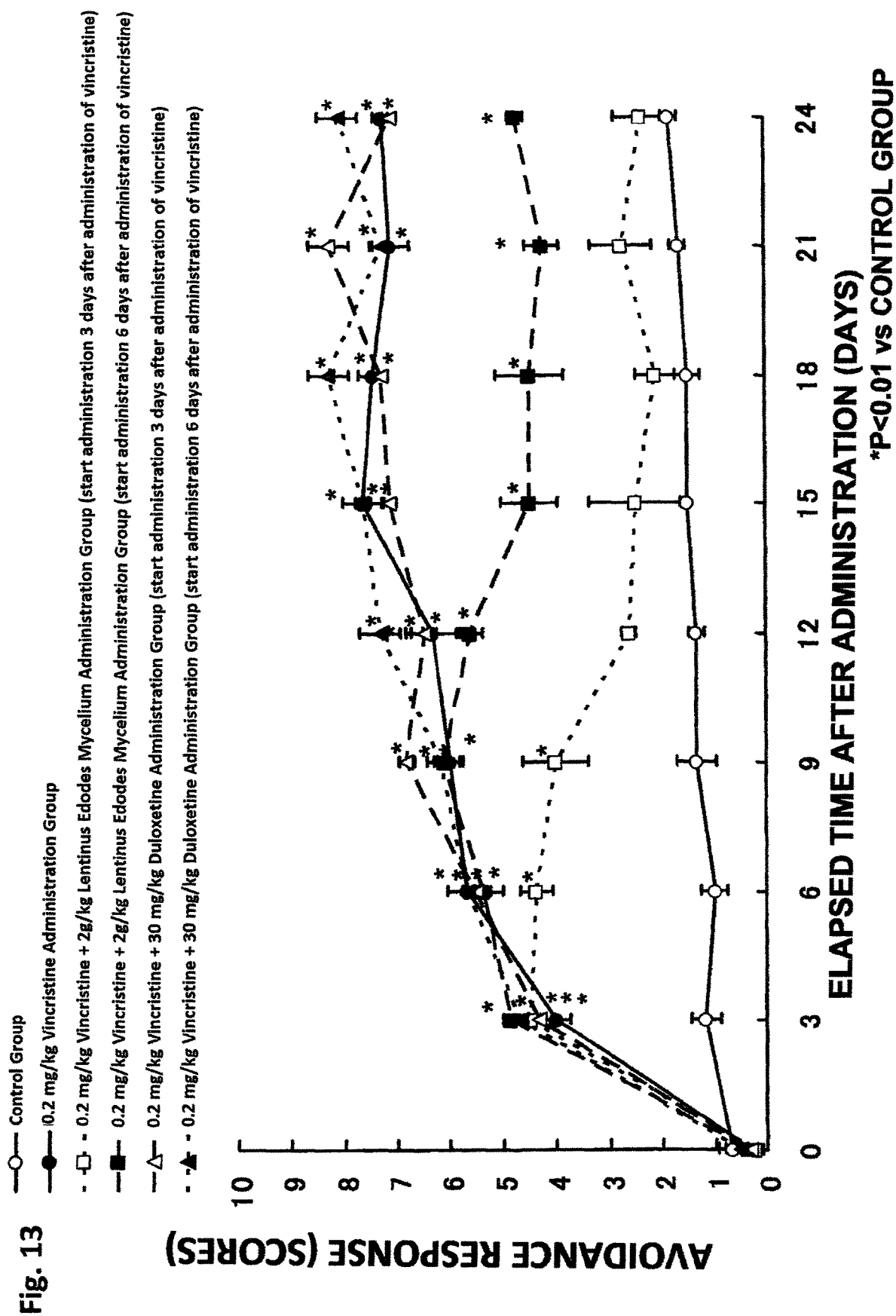
FIG. 13 is a diagram illustrating a result of the von Frey test in which the composition for ameliorating peripheral sensory neuropathy according to the present invention is administered after administration of vincristine.

Evaluation was performed in the same manner as in the test with oxaliplatin in Example 1. The result is shown in FIG. 13. Referring to FIG. 13, the horizontal axis indicates the elapsed time after administration (days) and the vertical axis indicates the avoidance response (scores). Open circles with a solid line represent the control group. Filled circles with a solid line represent the group in which only vincristine was administered. Open squares with a dash line and filled squares with a dash line represent the groups in which the *Lentinus edodes* mycelium extract was administered after the administration of vincristine ("*Lentinus edodes* mycelium extract 3-day delayed administration group" and "*Lentinus edodes* mycelium extract 6-day delayed administration group", respectively).

Further, open triangles with a dash line and filled triangles with a dash line represent the groups in which duloxetine was administered after the administration of vincristine ("duloxetine 3-day delayed administration group" and "duloxetine 6-day delayed administration group", respectively). When the difference with the control group was determined to be significant using a significance level of 5%, the data were marked by "*".

The avoidance response score significantly increased in the vincristine administration group (filled circles with a solid line) three day after the administration as compared with the control group (open circles with a solid line). This suggests that the peripheral sensory neuropathy was developed by the administration of vincristine. The *Lentinus edodes* mycelium extract 3-day delayed administration group (open squares with a dash line) had the lower avoidance score than that in the vincristine administration group (filled circles with a solid line) after the administration. The avoidance score in the *Lentinus edodes* mycelium extract 3-day delayed administration group (open squares with a dash line) was recovered to the same level as that in the control (open circles with a solid line) on Day 12. Further, the *Lentinus edodes* mycelium extract 6-day delayed administration group (filled squares with a dash line) also maintained the clearly lower score than that in the vincristine administration group (filled circles with a solid line) on Day 12 or later. That is, the *Lentinus edodes* mycelium extract administered after the onset of the peripheral sensory neuropathy is still effective for inhibiting the symptom.

On the other hand, in the duloxetine 3-day delayed administration group (open triangles with a dash line), the avoidance score never became lower than that in the vincristine administration group (filled circles with a solid line) after the administration. The duloxetine 3-day delayed administration group (open triangles with a dash line) had almost the same score as that in the vincristine administration group (filled circles with a solid line). Further, the duloxetine 6-day delayed administration group (filled triangles with a dash line) showed the same tendency as that in the duloxetine 3-day delayed administration group (open triangles with a dash line). That is, this suggests that duloxetine does not significantly contribute to the inhibition of the peripheral sensory neuropathy.

It was found that the suppression of the decrease in the pain threshold was maintained even after finishing the administration of the *Lentinus edodes* mycelium extract (Day 23 or later) in the *Lentinus edodes* mycelium extract 3-day delayed administration group (open squares with a dash line) and the *Lentinus edodes* mycelium extract 6-day delayed administration group.

(3) Cold Plate Test

In the present test, the mice were divided into six groups by a difference in test objects. As in Example 1, male Balb/c mice of 6 to 7 weeks old were used. The mice were divided into a total of six groups, a control group, a vincristine administration group, two different vincristine and *Lentinus edodes* mycelium extract administration groups (vincristine+*Lentinus edodes* mycelium extract administration groups), and two different vincristine and duloxetine administration groups (vincristine+duloxetine administration groups).

Vincristine was administered to each mouse once a day at a dose of 0.2 mg/kg. Further, the *Lentinus edodes* mycelium extract was administered to each mouse once a day at a dose of 2 g/kg three days or six days after the administration of vincristine. These groups are referred to as "*Lentinus edodes* mycelium extract 3-day delayed administration group" and "*Lentinus edodes* mycelium extract 6-day delayed administration group", respectively.

Further, groups in which duloxetine was administered after the administration of vincristine were prepared for comparison. Duloxetine was also administered once a day at a dose of 30 mg/kg three days or six days after the administration of vincristine. These groups are referred to as "duloxetine 3-day delayed administration group" and "duloxetine 6-day delayed administration group", respectively.

Figure 14:
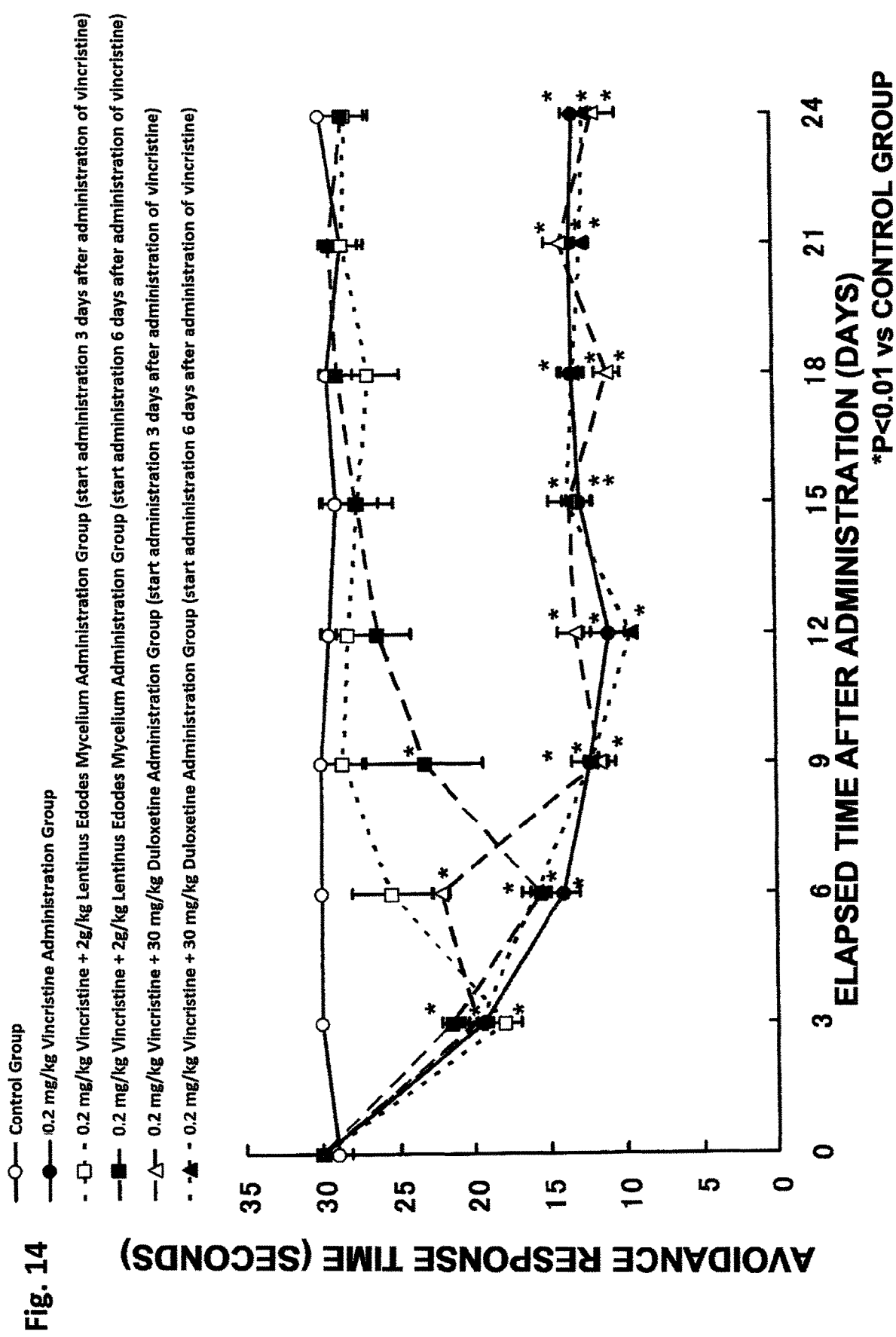
FIG. 14 is a diagram illustrating a result of the cold plate test in which the composition for ameliorating peripheral sensory neuropathy according to the present invention is administered after administration of vincristine.

Evaluation was performed in the same manner as in the test with oxaliplatin in Example 1. The result is shown in FIG. 14. Referring to FIG. 14, the horizontal axis indicates the elapsed time after administration (days) and the vertical axis indicates the avoidance response time (seconds). Open circles with a solid line represent the control group. Filled circles with a solid line represent the group in which only vincristine was administered. Open squares with a dash line and filled squares with a dash line represent the groups in which the *Lentinus edodes* mycelium extract was administered after the administration of vincristine ("*Lentinus edodes* mycelium extract 3-day delayed administration group" and "*Lentinus edodes* mycelium extract 6-day delayed administration group", respectively).

Further, open triangles with a dash line and filled triangles with a dash line represent the groups in which duloxetine was administered after the administration of vincristine ("duloxetine 3-day delayed administration group" and "duloxetine 6-day delayed administration group", respectively). When the difference with the control group was determined to be significant using a significance level of 5%, the data were marked by "*".

Referring to FIG. 14, on Day 3 in the test, the latency to the cold stimulation of the cold plate was significantly reduced in the vincristine administration group (filled circles with a solid line). This suggests that the peripheral sensory neuropathy was developed by vincristine as seen in the von Frey test. The latency in the *Lentinus edodes* mycelium extract 3-day delayed administration group (open squares with a dash line) became clearly longer than that in the vincristine administration group (filled circles with a solid line) after the administration. The latency in the *Lentinus edodes* mycelium extract 3-day delayed administration group (open squares with a dash line) was recovered to the same level as that in the control (open circles with a solid line) on Day 9 or later. Further, the latency in the *Lentinus edodes* mycelium extract 6-day delayed administration group (filled squares with a dash line) also became longer after the administration, and was recovered to the same level as that in the control (open circles with a solid line) on Day 18 or later.

On the other hand, the latency in the duloxetine 3-day delayed administration group (open triangles with a dash line) never became longer than that in the vincristine administration group (filled circles with a solid line) after the administration. The latency in the duloxetine 3-day delayed administration group was almost the same as that in the vincristine administration group (filled circles with a solid line). Further, the duloxetine 6-day delayed administration group (filled triangles with a dash line) showed the same tendency as that in the duloxetine 3-day delayed administration group (open triangles with a dash line). That is, this suggests that duloxetine does not significantly contribute to the inhibition of the peripheral sensory neuropathy (the cold hypersensitivity).

As described above, when used with the anticancer drug (vincristine), the *Lentinus edodes* mycelium extract according to the present invention can not only inhibit the peripheral sensory neuropathy, but also serve as the composition for treating peripheral sensory neuropathy (the medical composition for treating peripheral sensory neuropathy) that alleviates the symptom of the peripheral sensory neuropathy once developed.

(Example 8) <Treatment Effect on Peripheral Sensory Neuropathy Induced by Bortezomib in Mice>

The treatment effect of the *Lentinus edodes* mycelium extract of the present invention on hyperesthesia such as allodynia to mechanical stimulation and paresthesia to cold stimulation induced by administration of bortezomib as the anticancer drug was examined. The anticancer drug, bortezomib, was administered to mice to induce the peripheral sensory neuropathy, and then, the *Lentinus edodes* mycelium extract of the present invention was orally administered to the mice to perform the same tests (the cold plate test and the von Frey test) as those in Example 1.

(1) Administration of Test Object

In the present test, the mice were divided into six groups by a difference in test objects. As in Example 1, male Balb/c mice of 6 to 7 weeks old were used. The mice were divided into a total of six groups, a control group, a bortezomib administration group, two different bortezomib and *Lentinus edodes* mycelium extract administration groups (bortezomib+*Lentinus edodes* mycelium extract administration groups), and two different bortezomib and duloxetine administration groups (bortezomib+duloxetine administration groups).

Bortezomib was administered to each mouse once a day at a dose of 1 mg/kg. Further, the *Lentinus edodes* mycelium extract was administered to each mouse once a day at a dose of 2 g/kg three days or six days after the administration of bortezomib. These groups are referred to as "*Lentinus edodes* mycelium extract 3-day delayed administration group" and "*Lentinus edodes* mycelium extract 6-day delayed administration group", respectively. Further, groups in which duloxetine was administered after the administration of bortezomib were prepared for comparison.

Duloxetine was also administered once a day at a dose of 30 mg/kg three days or six days after the administration of bortezomib. These groups are referred to as "duloxetine 3-day delayed administration group" and "duloxetine 6-day delayed administration group", respectively.

Further, the number of times of administration was set to once a week (on Day 0, Day 7, Day 14, and Day 21) for bortezomib and daily from the administration start date (from Day 3 or Day 6 to Day 23) for the *Lentinus edodes* mycelium extract and duloxetine in both the von Frey test and the cold plate test below.

(2) Von Frey Test

Figure 15:
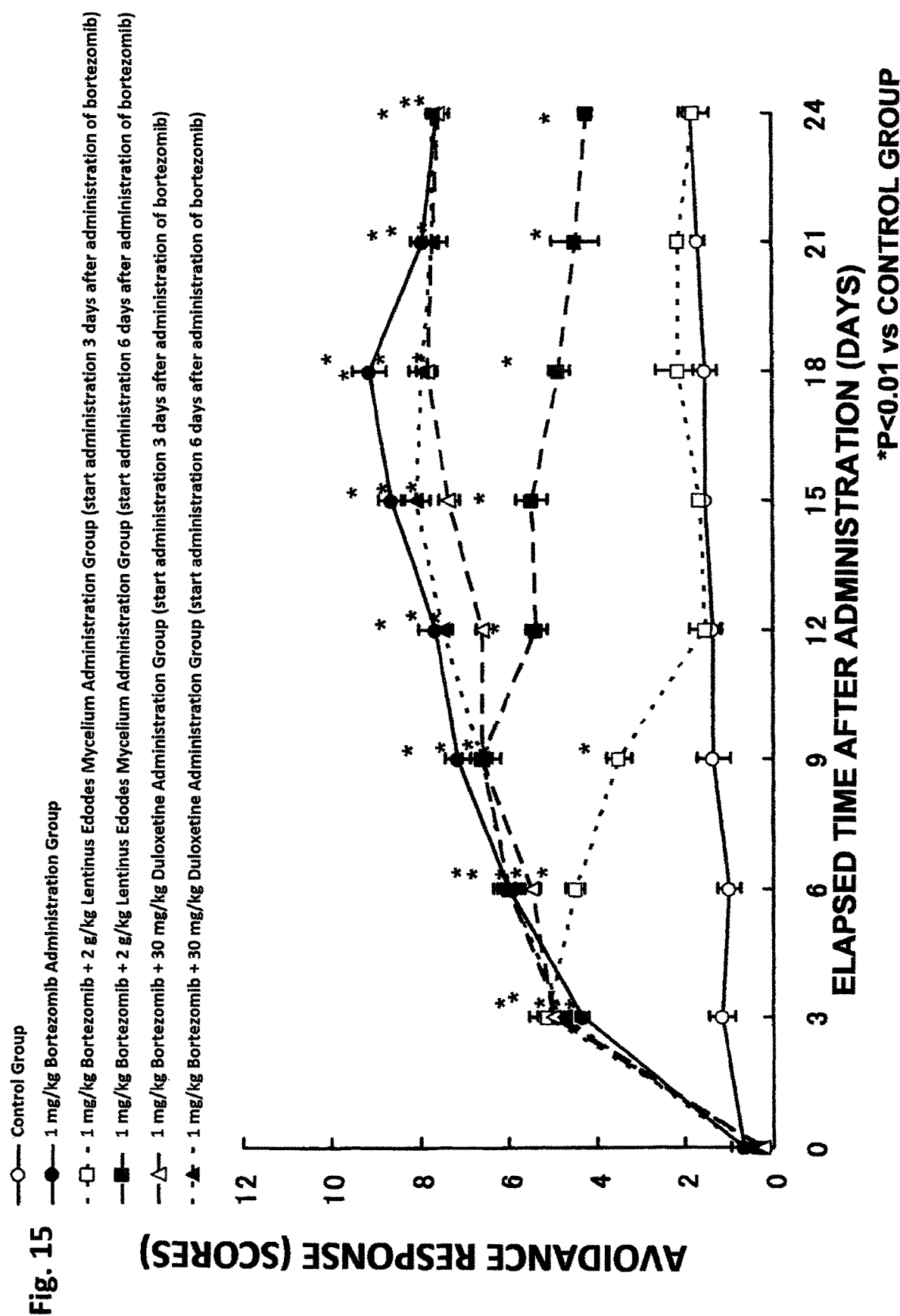
FIG. 15 is a diagram illustrating a result of the von Frey test in which the composition for ameliorating peripheral sensory neuropathy according to the present invention is administered after administration of bortezomib.

Evaluation was performed in the same manner as in the test with oxaliplatin in Example 1. The result is shown in FIG. 15. Referring to FIG. 15, the horizontal axis indicates the elapsed time after administration (days) and the vertical axis indicates the avoidance response (scores). Open circles with a solid line represent the control group. Filled circles with a solid line represent the group in which only bortezomib was administered. Open squares with a dash line and filled squares with a dash line represent the groups in which the *Lentinus edodes* mycelium extract was administered after the administration of bortezomib ("*Lentinus edodes* mycelium extract 3-day delayed administration group" and "*Lentinus edodes* mycelium extract 6-day delayed administration group", respectively).

Further, open triangles with a dash line and filled triangles with a dash line represent the groups in which duloxetine was administered after the administration of bortezomib ("duloxetine 3-day delayed administration group" and "duloxetine 6-day delayed administration group", respectively). When the difference with the control group was determined to be significant using a significance level of 5%, the data were marked by "*".

The avoidance response score significantly increased in the bortezomib administration group (filled circles with a solid line) three day after the administration as compared with the control group (open circles with a solid line). This suggests that the peripheral sensory neuropathy was developed by the administration of bortezomib. The *Lentinus edodes* mycelium extract 3-day delayed administration group (open squares with a dash line) had the lower avoidance score than that in the bortezomib administration group (filled circles with a solid line) after the administration. The avoidance score in the *Lentinus edodes* mycelium extract 3-day delayed administration group (open squares with a dash line) was recovered to the same level as that in the control (open circles with a solid line) on Day 12. Further, the *Lentinus edodes* mycelium extract 6-day delayed administration group (filled squares with a dash line) also maintained the clearly lower score than that in the bortezomib administration group (filled circles with a solid line) on Day 12 or later. That is, the *Lentinus edodes* mycelium extract administered after the onset of the peripheral sensory neuropathy is still effective for inhibiting the symptom.

On the other hand, in the duloxetine 3-day delayed administration group (open triangles with a dash line), the avoidance score never became lower than that in the bortezomib administration group (filled circles with a solid line) after the administration. The duloxetine 3-day delayed administration group (open triangles with a dash line) had almost the same score as that in the bortezomib administration group (filled circles with a solid line). Further, the duloxetine 6-day delayed administration group (filled triangles with a dash line) showed the same tendency as that in the duloxetine 3-day delayed administration group (open triangles with a dash line). That is, this suggests that duloxetine does not significantly contribute to the inhibition of the peripheral sensory neuropathy.

It was found that the suppression of the decrease in the pain threshold was maintained even after finishing the administration of the *Lentinus edodes* mycelium extract (Day 23 or later) in the *Lentinus edodes* mycelium extract 3-day delayed administration group (open squares with a dash line) and the *Lentinus edodes* mycelium extract 6-day delayed administration group.

(3) Cold Plate Test

In the present test, the mice were divided into six groups by a difference in test objects. As in Example 1, male Balb/c mice of 6 to 7 weeks old were used. The mice were divided into a total of six groups, a control group, a bortezomib administration group, two different bortezomib and *Lentinus edodes* mycelium extract administration groups (bortezomib+*Lentinus edodes* mycelium extract administration groups), and two different bortezomib and duloxetine administration groups (bortezomib+duloxetine administration groups).

Bortezomib was administered to each mouse once a day at a dose of 1 mg/kg. Further, the *Lentinus edodes* mycelium extract was administered to each mouse once a day at a dose of 2 g/kg three days or six days after the administration of bortezomib. These groups are referred to as "*Lentinus edodes* mycelium extract 3-day delayed administration group" and "*Lentinus edodes* mycelium extract 6-day delayed administration group", respectively.

Further, groups in which duloxetine was administered after the administration of bortezomib were prepared for comparison. Duloxetine was also administered once a day at a dose of 30 mg/kg three days or six days after the administration of bortezomib. These groups are referred to as "duloxetine 3-day delayed administration group" and "duloxetine 6-day delayed administration group", respectively.

Figure 16:
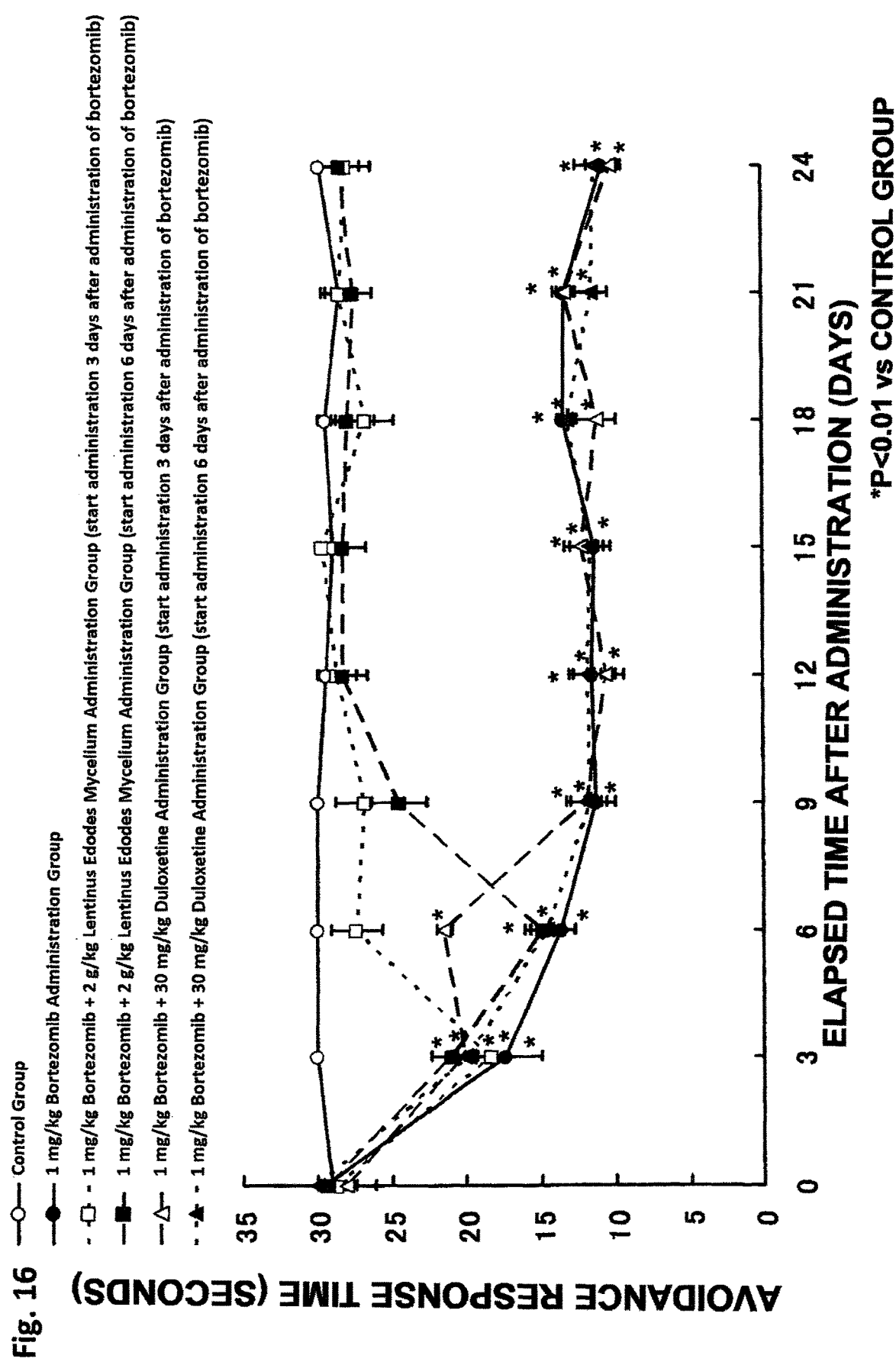
FIG. 16 is a diagram illustrating a result of the cold plate test in which the composition for ameliorating peripheral sensory neuropathy according to the present invention is administered after administration of bortezomib.

Evaluation was performed in the same manner as in the test with oxaliplatin in Example 1. The result is shown in FIG. 16. Referring to FIG. 14, the horizontal axis indicates the elapsed time after administration (days) and the vertical axis indicates the avoidance response time (seconds). Open circles with a solid line represent the control group. Filled circles with a solid line represent the group in which only bortezomib was administered. Open squares with a dash line and filled squares with a dash line represent the groups in which the *Lentinus edodes* mycelium extract was administered after the administration of bortezomib ("*Lentinus edodes* mycelium extract 3-day delayed administration group" and "*Lentinus edodes* mycelium extract 6-day delayed administration group", respectively).

Further, open triangles with a dash line and filled triangles with a dash line represent the groups in which duloxetine was administered after the administration of bortezomib ("duloxetine 3-day delayed administration group" and "duloxetine 6-day delayed administration group", respectively). When the difference with the control group was determined to be significant using a significance level of 5%, the data were marked by "*".

Referring to FIG. 16, on Day 3 in the test, the latency to the cold stimulation of the cold plate was significantly reduced in the bortezomib administration group (filled circles with a solid line). This suggests that the peripheral sensory neuropathy was developed by bortezomib as seen in the von Frey test. The latency in the *Lentinus edodes* mycelium extract 3-day delayed administration group (open squares with a dash line) became clearly longer than that in the bortezomib administration group (filled circles with a solid line) after the administration. The latency in the *Lentinus edodes* mycelium extract 3-day delayed administration group (open squares with a dash line) was recovered to the same level as that in the control (open circles with a solid line) on Day 12 or later. Further, the latency in the *Lentinus edodes* mycelium extract 6-day delayed administration group (filled squares with a dash line) also became longer after the administration, and was recovered to the same level as that in the control (open circles with a solid line) on Day 12 or later.

On the other hand, the latency in the duloxetine 3-day delayed administration group (open triangles with a dash line) never became longer than that in the bortezomib administration group (filled circles with a solid line) after the administration. The latency in the duloxetine 3-day delayed administration group (open triangles with a dash line) was almost the same as that in the bortezomib administration group (filled circles with a solid line). Further, the duloxetine 6-day delayed administration group (filled triangles with a dash line) showed the same tendency as that in the duloxetine 3-day delayed administration group (open triangles with a dash line). That is, this suggests that duloxetine does not significantly contribute to the inhibition of the peripheral sensory neuropathy (the cold hypersensitivity).

As described above, when used with the anticancer drug (bortezomib), the *Lentinus edodes* mycelium extract according to the present invention can not only inhibit the peripheral sensory neuropathy, but also serve as the composition for treating peripheral sensory neuropathy (the medical composition for treating peripheral sensory neuropathy) that alleviates the symptom of the peripheral sensory neuropathy once developed.

Example 9

It was suggested that the *Lentinus edodes* mycelium extract according to the present invention could potentially ameliorate the symptom of the peripheral sensory neuropathy with Grade 2 or higher in the clinical trials for treating the colorectal cancer. The subjects and methods will be described below.

The subjects were patients undergoing the XELOX therapy as a postoperative adjuvant chemotherapy for colorectal cancer with Stage After randomly allocated, the patients were administered with a tablet formulated with LEM (the *Lentinus edodes* mycelium according to the present invention) (1,800 mg/day) or a placebo tablet every day for 6 months of the postoperative adjuvant chemotherapy. Oxaliplatin (L-OHP) was administered at a dose of 130 mg/m$^2$ on the first day of each 8 cycle for the 6 months.

As an evaluation item, the onset of the side effect, that is, the symptom of the peripheral sensory neuropathy, was evaluated according to the criteria of CTCAE ver.4. The safety analysis set included 46 cases (LEM group: 24 cases, placebo group: 22 cases) capable of initiating the protocol treatment.

Regarding the onset of the symptom of the peripheral sensory neuropathy (PSN) with Grade 2 or higher, the LEM group tended to have a better outcome (LEM group: 16.7% and placebo group: 27.3%). Further, regarding the median time to the onset of PSN with Grade 2 or higher, the LEM group tended to have the longer median time (LEM grope: 158 days and placebo group: 107 days).

From the above results, it can be concluded that the *Lentinus edodes* mycelium extract ameliorates (prevents and treats) the symptom of the peripheral nervous erethism. Further, it was shown that the effect could be exerted at a dose of 1 g/kg/day or more in mice.

INDUSTRIAL APPLICABILITY

The composition for ameliorating peripheral sensory neuropathy according to the present invention can be used to relieve, alleviate, or prevent the peripheral sensory neuropathy. Further, the composition can be used to treat the peripheral sensory neuropathy once developed. In particular, the composition can be preferably used to relieve, alleviate, prevent, or treat the peripheral sensory neuropathy caused by taking the DNA replication inhibitor (the platinum-based anticancer drug (oxaliplatin, etc.) and the alkylating agent), the microtubule-stabilizing agent (paclitaxel, etc.), the microtubule polymerization inhibitor (vincristine, etc.), or the proteasome inhibitor (bortezomib, etc.).

What is claimed is:
1. A method of ameliorating peripheral sensory neuropathy, comprising:
   administering a composition including a *Lentinus edodes* mycelium extract to a patient having peripheral sensory neuropathy, thereby ameliorating the peripheral sensory neuropathy, wherein the peripheral sensory neuropathy is induced after administration of an anticancer drug.

2. The method of ameliorating peripheral sensory neuropathy according to claim 1, wherein the anticancer drug is at least one selected from a DNA replication inhibitor, a microtubule-stabilizing agent, a microtubule polymerization inhibitor, and a proteasome inhibitor.

3. The method of ameliorating peripheral sensory neuropathy according to claim 1, wherein the anticancer drug is a platinum-based anticancer drug.

4. A method of treating peripheral sensory neuropathy, comprising:
administering a medical composition including a *Lentinus edodes* mycelium extract to a patient having peripheral sensory neuropathy, thereby treating the peripheral sensory neuropathy, wherein the peripheral sensory neuropathy is induced after administration of an anticancer drug.

5. A method of ameliorating peripheral sensory neuropathy, comprising:
administering a processed food including a *Lentinus edodes* mycelium extract to a patient having peripheral sensory neuropathy, thereby ameliorating the peripheral sensory neuropathy, wherein the peripheral sensory neuropathy is induced after administration of an anticancer drug.

6. The method of ameliorating peripheral sensory neuropathy according to claim 2, wherein the DNA replication inhibitor is a platinum-based anticancer drug.

7. The method of ameliorating peripheral sensory neuropathy according to claim 1, wherein the composition is administered orally.

8. The method of ameliorating peripheral sensory neuropathy according to claim 1, wherein the patient is a human patient.

* * * * *